(12) United States Patent
Eakle et al.

(10) Patent No.: US 7,300,790 B2
(45) Date of Patent: Nov. 27, 2007

(54) TRANSGENIC ANIMALS EXPRESSING TRANSDOMINANT NEGATIVE RETROVIRAL NUCLEIC ACIDS AND PROTEINS

(75) Inventors: Kurt Eakle, Prairie du Sac, WI (US); Thomas Hope, Oak Brook, IL (US); Eun-A Choi, Chicago, IL (US); Jane Homan, Hillpoint, WI (US); Robert D. Bremel, Hillpoint, WI (US)

(73) Assignee: ioGenetics, LLC, Madison, WI (US)

( * ) Notice: Subject to any disclaimer, the term of this patent is extended or adjusted under 35 U.S.C. 154(b) by 447 days.

(21) Appl. No.: 10/764,201

(22) Filed: Jan. 23, 2004

(65) Prior Publication Data

US 2004/0253581 A1    Dec. 16, 2004

Related U.S. Application Data

(60) Provisional application No. 60/442,047, filed on Jan. 23, 2003.

(51) Int. Cl.
*C12P 1/00* (2006.01)
*C12P 37/04* (2006.01)

(52) U.S. Cl. .................... 435/320.1; 435/71.2; 435/41; 435/70.1

(58) Field of Classification Search .................... None
See application file for complete search history.

(56) References Cited

U.S. PATENT DOCUMENTS

| | | | |
|---|---|---|---|
| 5,871,958 A | 2/1999 | Cullen | |
| 6,162,898 A | 12/2000 | Cullen | |
| 2003/0083290 A1* | 5/2003 | Kingsman et al. | 514/44 |

FOREIGN PATENT DOCUMENTS

EP    0406557    5/1990

OTHER PUBLICATIONS

Oroszlan et al., Primary structure analysis of the major internal protein p24 of human type C T-cell leukemia virus. Proc Natl Acad Sci U S A. Feb. 1982;79(4):1291-4.*
Pollari, F.L., et al., "Effects of bovine leukemia virus infection on production and reproduction in dairy cattle," Can. J. Vet. Res., 56(4):289-95 (1992).
Hidaka et al., "Post-transcriptional regulator (rex) of HTLV-1 initiates expression of viral structural proteins but suppresses expression of regulatory proteins," EMBO J 7:519 (1988).
Malim, M.H., et al., "Immunodeficiency virus rev trans-activator modulates the expression of the viral regulatory genes," Nature, 335:181 (1988).
Rimsky, L., et al., "Functional replacement of the HIV-1 rev protein by the HTLV-1 rex protein," Nature, 335:738 (1988).
Green, P.L., et al., The Retroviridae, p. 227-311, vol. 3, Eds. Levy, J.A., Plenum Press, New York, N.Y., (1994).

Ghysdael, K., et al., "Bovine leukemia virus," Current Topics in Microbiology and Immunology 112:1 (1984) Gree, P.L., The Retroviridae, p. 227-311, vol. 3, Eds. Levy, J.A., Plenum Press, New York, N.Y., (1994).
Orlik, O., and Splitter G.A., "Progression to persistent lymphocytosis and tumor development in bovine leukemia virus (BLV)-infected cattle correlates with impaired proliferation of CD4+ T cells in response to gag- and env- encoded BLV proteins," J. Virol., 70(11):7584 (1996).
Elovaara, I., et al., "High human T cell lymphotropic virus type 1 (HTLV-1)-specific precursor cytotoxic T lymphocyte frequencies in patients with HTLV-1-associated neurological disease," J. Exp. Med., 177:1567 (1993).
Lassauzet, ML, et al., "Factors associated with transmission of bovine leukemia virus by contact in cows on a California dairy," Amer. J. Epidemiol, 133:164-76 (1991).
Lassauzet, M.L., et al., "Effect of brucellosis vaccination and dehorning on transmission of bovine leukemia virus in heifers on a California dairy," Can. J. Vet. Res. 54:184-189 (1990).
Buxton, B.A., and Schultz, R.D., "Factors affecting the infectivity of lymphocytes from cattle with bovine leukosis virus," Can. J. Comp. Med., 48(4):365-369 (1984).
Herskowitz, I., Nature 329:317 (1987).
Hope, I.A., and Struhl, K., "Functional dissection of a eukaryotic transcriptional activator protein, GCN4 of yeast," Cell 46:885 (1986).
Gentz, R., et al., "Parallel association of Fos and Jun leucine zippers juxtaposes DNA binding domains," Science 243:1695 (1989).
Triezenberg, S.J., et al., Gen. & Devel., 2:718 (1988).
Friedman A.D., et al., "Functional dissection of VP16, tha transactivator of herpes simplex virus immediate early gene expression," Nature, 335:452 (1988).
Wachsman, V., et al., "HTLV x gene mutants exhibit novel transcriptional regulatory phenotypes," Science 235:674 (1987).
Green, M., et al., "Mutational analysis of HIV-1 Tat minimal domain peptides: identification of trans-dominant mutants that suppress HIV-LTR-driven gene expression," Cell 58:215 (1989).
Trono, D., et al., "HIV-1 Gag mutants can dominantly interfere with the replication of the wild-type virus," Cell 59:113 (1989).
Orlik, O., and Splitter G.A., "Optimization of lymphocyte proliferation assay for cells with high spontaneous proliferation in vitro: CD4+ T cell proliferation in bovine leukemia virus infected animals with persistent lymphocytosis," J. Immunol. Methods 199:159 (1996).
Kimata, J.J., et al., "The mitogenic activity of human T-cell leukemia virus type I is T-cell associated and requires the CD2/LFA-3 activation pathway," J. Virol., 67:3134 (1993).
Boris-Lawrie et al., "In vivo study of genetically simplified bovine leukemia virus derivatives that lack tax and rex," J Virol 71(2):1514-20 (1997).
Gatei M.H., et al., "Experimental infection of sheep with bovine leukemia virus: infectivity of blood, nasal and saliva secretions," Zentralbl Veterinarmed, (B) 36(9):652-60 (1989).

* cited by examiner

*Primary Examiner*—Joseph Woitach
*Assistant Examiner*—Maria Leavitt
(74) *Attorney, Agent, or Firm*—Casimir Jones, S.C.

(57) ABSTRACT

The present invention relates to non-vaccinal and non-pharmacologic compositions and methods for controlling complex retroviral infections. In particular, the present invention provides transgenic animals expressing a transdominant negative Rex gene product that inhibits retroviral replication.

11 Claims, 23 Drawing Sheets

Figure 1 A, B, and C
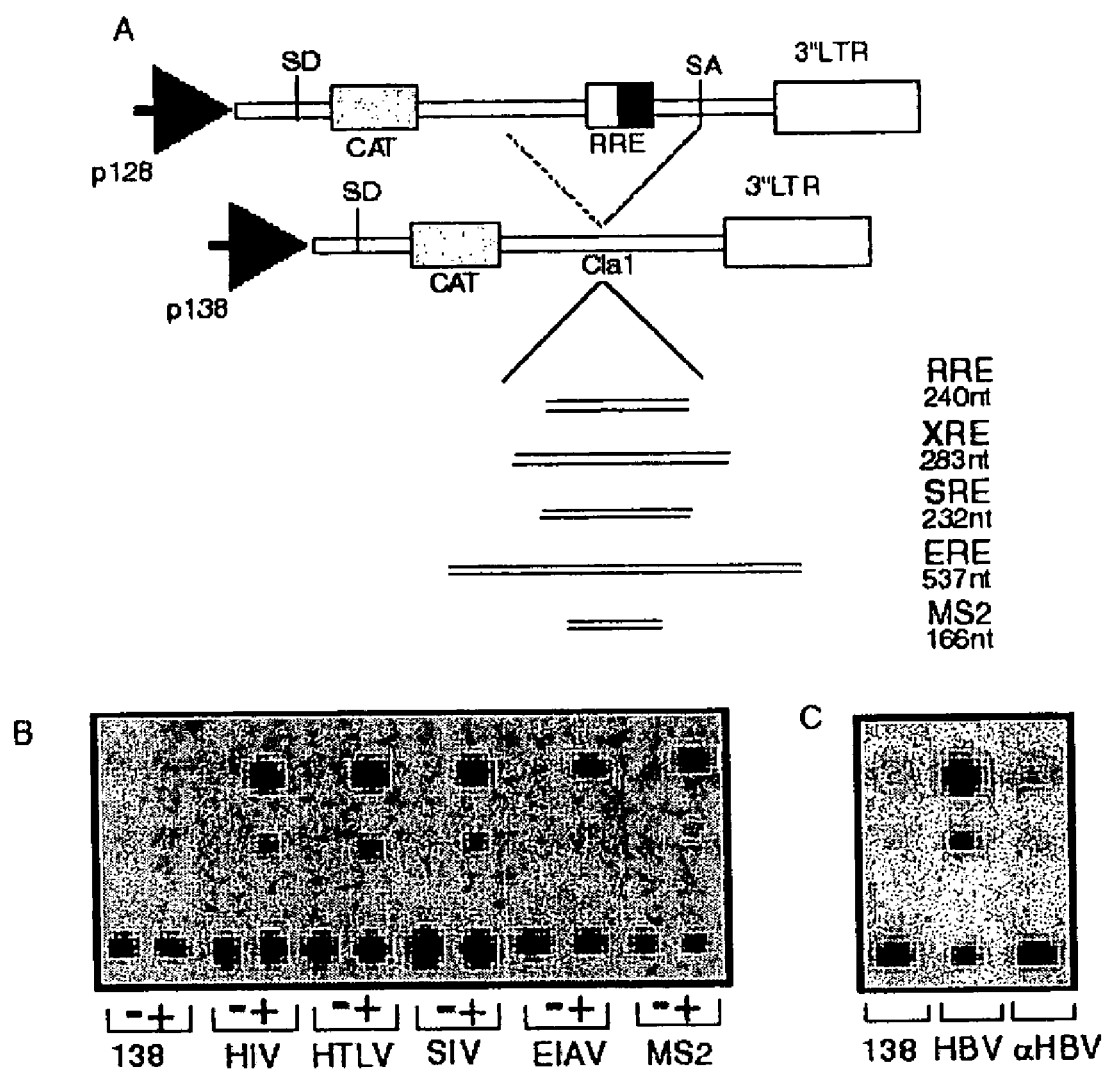

Figure 2

```
HTLV :  1 MPKTRRRPRRSQRKRPPTPW------PTSQGLDRVFFSDTQSTCLETVYKATGAPSLGD  53
          RNA binding domain and NLS
BLV  :  1 MPKERRSRRRPQ---PIIRWQVLLVGGPTLYMPARPWFCPMMSPSMP-----GAPSAGP  51

HTLV :54 YVRPAYIVTPYWPPVQSIRSPGTPSMDALSAQLYSSLSLD--SPPSPPREPLRPSRSLP-RQ 112
                                    NES
BLV  : 52 MSDSNSKGSTPRSPARPTVSTGPP-MDDLAASMER-CSLDCMSPRPAPKGPDDSGSTAPFRP 111

HTLV: 113 SLIQPPTFH-PPSSRP-----CANTP 132
          Dominant Negative Mutation
BLV  : 112 FALSPARFHFPPSSGPPSSPTNANCP 137
```

Figure 3

Figure 4

Figure 5 A, B, C, and D
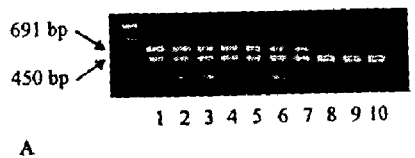
A
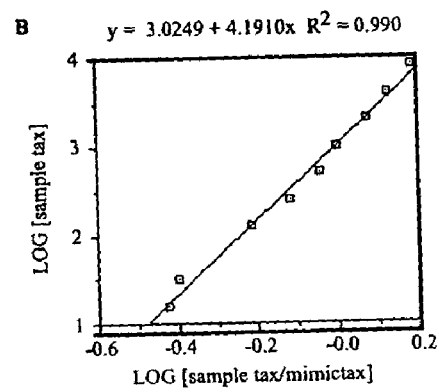
B  y = 3.0249 + 4.1910x  $R^2 = 0.990$
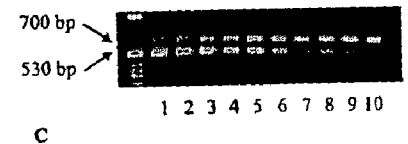
C
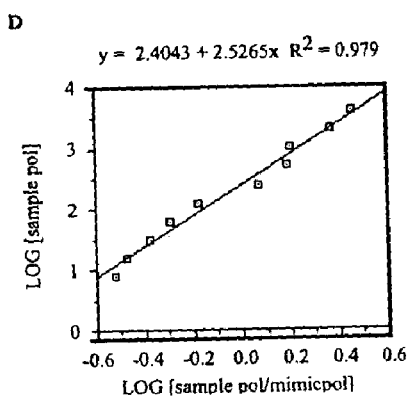
D  y = 2.4043 + 2.5265x  $R^2 = 0.979$

Figure 6

SEQ ID NO:1, Brex wild-type DNA Seqence

```
ATG CCT AAA AAA CGA CGG TCC CGA AGA CGC CCA CAA CCG ATC ATC AGA TGG CAA
GTG TTG TTG GTT GGG GGC CCC ACT CTC TAC ATG CCT GCC CGG CCC TGG TTT TGT
CCA ATG ATG TCA CCA TCG ATG CCT GGT GCC CCC TCT GCG GGC CCC ATG AGC GAC
TCC AAT TCG AAA GGA TCG ACA CCA CGC TCA CCT GCG AGA CCC ACC GTA TCA ACT
GGA CCG CCG ATG GAC GAC CTT GCG GCC TCA ATG GAA CGT TGT TCC CTC GAC TGC
ATG TCT CCG AGA CCC GCC CCC AAG GGC CCC GAC GAC TCT GGA TCA ACT GCC CCC
TTC CGG CCG TTC GCG CTC AGC CCG GCC CGG TTT CAC TTT CCC CCT TCG AGC GGT
CCC CCT TCC AGC CCT ACC AAT GCC AAT TGC CCT CGG CCT CTA GCG ACG GTT GCC
CCA TTA TCG GGC ACG GCC TTC TTC CCT GGA ACA ACT TAG
```

Figure 7

SEQ ID NO:2, Brex wild-type amino acid sequence

```
Met Pro Lys Lys Arg Arg Ser Arg Arg Pro Gln Pro Ile Ile Arg Trp Gln
Val Leu Leu Val Gly Gly Pro Thr Leu Tyr Met Pro Ala Arg Pro Trp Phe Cys
Pro Met Met Ser Pro Ser Met Pro Gly Ala Pro Ser Ala Gly Pro Met Ser Asp
Ser Asn Ser Lys Gly Ser Thr Pro Arg Ser Pro Ala Arg Pro Thr Val Ser Thr
Gly Pro Pro Met Asp Asp Leu Ala Ala Ser Met Glu Arg Cys Ser Leu Asp Cys
Met Ser Pro Arg Pro Ala Pro Lys Gly Pro Asp Asp Ser Gly Ser Thr Ala Pro
Phe Arg Pro Phe Ala Leu Ser Pro Ala Arg Phe His Phe Pro Pro Ser Ser Gly
Pro Pro Ser Ser Pro Thr Asn Ala Asn Cys Pro Arg Pro Leu Ala Thr Val Ala
Pro Leu Ser Gly Thr Ala Phe Phe Pro Gly Thr Thr
```

Figure 8

SEQ ID NO:3, M7 DNA sequence

```
ATG CCT AAA AAA CGA CGG TCC CGA AGA CGC CCA CAA CCG ATC ATC AGA TGG CAA
GTG TTG TTG GTT GGG GGC CCC ACT CTC TAC ATG CCT GCC CGG CCC aga tct TGT
CCA ATG ATG TCA CCA TCG ATG CCT GGT GCC CCC TCT GCG GGC CCC ATG AGC GAC
TCC AAT TCG AAA GGA TCG ACA CCA CGC TCA CCT GCG AGA CCC ACC GTA TCA ACT
GGA CCG CCG ATG GAC GAC CTT GCG GCC TCA ATG GAA CGT TGT TCC CTC GAC TGC
ATG TCT CCG AGA CCC GCC CCC AAG GGC CCC GAC GAC TCT GGA TCA ACT GCC CCC
TTC CGG CCG TTC GCG CTC AGC CCG GCC CGG TTT CAC TTT CCC CCT TCG AGC GGT
CCC CCT TCC AGC CCT ACC AAT GCC AAT TGC CCT CGG CCT CTA GCG ACG GTT GCC
CCA TTA TCG GGC ACG GCC TTC TTC CCT GGA ACA ACT TAG
```

Figure 9

SEQ ID NO:4, M8 DNA sequence

ATG CCT AAA AAA CGA CGG TCC CGA AGA CGC CCA CAA CCG ATC ATC AGA TGG CAA
GTG TTG TTG GTT GGG GGC CCC ACT CTC TAC ATG CCT GCC CGG CCC TGG TTT TGT
CCa gat ctG TCA CCA TCG ATG CCT GGT GCC CCC TCT GCG GGC CCC ATG AGC GAC
TCC AAT TCG AAA GGA TCG ACA CCA CGC TCA CCT GCG AGA CCC ACC GTA TCA ACT
GGA CCG CCG ATG GAC GAC CTT GCG GCC TCA ATG GAA CGT TGT TCC CTC GAC TGC
ATG TCT CCG AGA CCC GCC CCC AAG GGC CCC GAC GAC TCT GGA TCA ACT GCC CCC
TTC CGG CCG TTC GCG CTC AGC CCG GCC CGG TTT CAC TTT CCC CCT TCG AGC GGT
CCC CCT TCC AGC CCT ACC AAT GCC AAT TGC CCT CGG CCT CTA GCG ACG GTT GCC
CCA TTA TCG GGC ACG GCC TTC TTC CCT GGA ACA ACT TAG

Figure 10

SEQ ID NO:5, M4 DNA sequence

ATG CCT AAA AAA CGA CGG TCC CGA AGA CGC CCA CAA CCG ATC ATC AGA TGG CAA
GTG TTG TTG GTT GGG GGC CCC ACT CTC TAC ATG CCT GCC CGG CCC TGG TTT TGT
CCA ATG ATG TCA CCA TCG ATG CCT GGT GCC CCC TCT GCG GGC CCC ATG AGC GAC
TCC AAT TCG AAA GGA TCG ACA CCA CGC TCA CCT GCG AGA CCC ACC GTA TCA ACT
GGA CCG CCG ATG GAC GAC CTT GCG GCC TCA ATG GAA CGT TGT TCC CTC GAC TGC
ATG TCT CCG AGA CCC GCC CCC AAG GGC CCC GAC GAC TCT GGA TCA ACT GCC CCC
TTC CGG CCG TTC GCG CTC AGC CCG GCC CGG TTa gat ctT CCC CCT TCG AGC GGT
CCC CCT TCC AGC CCT ACC AAT GCC AAT TGC CCT CGG CCT CTA GCG ACG GTT GCC
CCA TTA TCG GGC ACG GCC TTC TTC CCT GGA ACA ACT TAG

Figure 11

SEQ ID NO:6, M4Δ7 DNA sequence

ATG CCT AAA AAA CGA CGG TCC CGA AGA CGC CCA CAA CCG ATC ATC AGA TGG CAA
GTG TTG TTG GTT GGG GGC CCC ACT CTC TAC ATG CCT GCC CGG CCC AGA TCT GTC
ACC ATC GAT GCC TGG TGC CCC CTC TGC GGG CCC CAT GAG CGA CTC CAA TTC GAA
AGG ATC GAC ACC ACG CTC ACC TGC GAG ACC CAC CGT ATC AAC TGG ACC GCC GAT
GGA CGA CCT TGC GGC CTC AAT GGA CGT TGT TCC TGA CTG CAT GTC TCC GAG
ACC GCC CCA AGG GCC CGA CGA CTC TGG ATC AAC TGC CCC TTC CGG CCG TTC
GCG CTC AGC CCG GCC GGT AGA TCT TCC CCT TCG AGC GGT CCC CCT TCA G
CCC TAC AAT GCA ATT GCC CTC GGC CTC TAG CGA CGG TGC CCC ATT ATC GGG
CAC GGC TTC TTC CCT GGA ACA ACT TAG TAC GCA TCC TGT CTC AGA AAA GTC
CTT ATA TTA AAT CAA ATG GGA CCT CGA GGG GGG CCC GAA TTC CGA TCT TGT
GAA GGA ACC TTA CTT CTG TGG TGT GAC ATA ATT GGA CAA CTA CCT ACA GAT
TTA AAG CTC TAA

Sequence and translation of M7Stop construct in the pRS expression plasmid

Figure 13

SEQ ID NO:8, M7 amino acid sequence

Met Pro Lys Lys Arg Arg Ser Arg Arg Arg Pro Gln Pro Ile Ile Arg Trp Gln
Val Leu Leu Val Gly Gly Pro Thr Leu Tyr Met Pro Ala Arg Pro Arg Ser Cys
Pro Met Met Ser Pro Ser Met Pro Gly Ala Pro Ser Ala Gly Pro Met Ser Asp
Ser Asn Ser Lys Gly Ser Thr Pro Arg Ser Pro Ala Arg Pro Thr Val Ser Thr
Gly Pro Pro Met Asp Asp Leu Ala Ala Ser Met Glu Arg Cys Ser Leu Asp Cys
Met Ser Pro Arg Pro Ala Pro Lys Gly Pro Asp Asp Ser Gly Ser Thr Ala Pro
Phe Arg Pro Phe Ala Leu Ser Pro Ala Arg Phe His Phe Pro Pro Ser Ser Gly
Pro Pro Ser Ser Pro Thr Asn Ala Asn Cys Pro Arg Pro Leu Ala Thr Val Ala
Pro Leu Ser Gly Thr Ala Phe Phe Pro Gly Thr Thr

Figure 14

SEQ ID NO:9, M8 amino acid sequence

Met Pro Lys Lys Arg Arg Ser Arg Arg Arg Pro Gln Pro Ile Ile Arg Trp Gln
Val Leu Leu Val Gly Gly Pro Thr Leu Tyr Met Pro Ala Arg Pro Trp Phe Cys
Pro Asp Leu Ser Pro Ser Met Pro Gly Ala Pro Ser Ala Gly Pro Met Ser Asp
Ser Asn Ser Lys Gly Ser Thr Pro Arg Ser Pro Ala Arg Pro Thr Val Ser Thr
Gly Pro Pro Met Asp Asp Leu Ala Ala Ser Met Glu Arg Cys Ser Leu Asp Cys
Met Ser Pro Arg Pro Ala Pro Lys Gly Pro Asp Asp Ser Gly Ser Thr Ala Pro
Phe Arg Pro Phe Ala Leu Ser Pro Ala Arg Phe His Phe Pro Pro Ser Ser Gly
Pro Pro Ser Ser Pro Thr Asn Ala Asn Cys Pro Arg Pro Leu Ala Thr Val Ala
Pro Leu Ser Gly Thr Ala Phe Phe Pro Gly Thr Thr

Figure 15

SEQ ID NO:10, M4 amino acid sequence

Met Pro Lys Lys Arg Arg Ser Arg Arg Arg Pro Gln Pro Ile Ile Arg Trp Gln
Val Leu Leu Val Gly Gly Pro Thr Leu Tyr Met Pro Ala Arg Pro Trp Phe Cys
Pro Met Met Ser Pro Ser Met Pro Gly Ala Pro Ser Ala Gly Pro Met Ser Asp
Ser Asn Ser Lys Gly Ser Thr Pro Arg Ser Pro Ala Arg Pro Thr Val Ser Thr
Gly Pro Pro Met Asp Asp Leu Ala Ala Ser Met Glu Arg Cys Ser Leu Asp Cys
Met Ser Pro Arg Pro Ala Pro Lys Gly Pro Asp Asp Ser Gly Ser Thr Ala Pro
Phe Arg Pro Phe Ala Leu Ser Pro Ala Arg Leu Asp Leu Pro Pro Ser Ser Gly
Pro Pro Ser Ser Pro Thr Asn Ala Asn Cys Pro Arg Pro Leu Ala Thr Val Ala
Pro Leu Ser Gly Thr Ala Phe Phe Pro Gly Thr Thr

Figure 16

SEQ ID NO:11, M4Δ7 amino acid sequence

Met Pro Lys Lys Arg Arg Ser Arg Arg Arg Pro Gln Pro Ile Ile Arg Trp Gln
Val Leu Leu Val Gly Gly Pro Thr Leu Tyr Met Pro Ala Arg Pro Arg Ser Val
Thr Ile Asp Ala Trp Cys Pro Leu Cys Gly Pro His Glu Arg Leu Gln Phe Glu
Arg Ile Asp Thr Thr Leu Thr Cys Glu Thr His Arg Ile Asn Trp Thr Ala Asp
Gly Arg Pro Cys Gly Leu Asn Gly Thr Leu Phe Pro Arg Leu His Val Ser Glu
Thr Arg Pro Gln Gly Pro Arg Arg Leu Trp Ile Asn Cys Pro Leu Pro Ala Val
Arg Ala Gln Pro Gly Pro Val Arg Ser Ser Pro Phe Glu Arg Ser Pro Phe Gln
Pro Tyr Gln Cys Gln Leu Pro Ser Ala Ser Ser Asp Gly Cys Pro Ile Ile Gly
His Gly Leu Leu Pro Trp Asn Asn Leu Val Thr His Pro Val Leu Arg Lys Val
Leu Ile Leu Asn Gln Met ▓▓▓▓▓▓▓▓▓▓▓▓▓▓▓▓▓▓▓▓▓▓▓▓▓▓ Asp Leu Cys
Glu Gly Thr Leu Leu Leu Trp Cys Asp Ile Ile Gly Gln Thr Thr Tyr Arg Asp
Leu Lys Leu

Figure 17

HTLV: 113 SLIQPPTFH-PPSSRP-----CANTP 132
Dominant Negative Mutation
BLV : 112 FALSPARFHFPPSSGPPSSPTNANCP 137

| | |
|---|---|
| M1 | AAA |
| M2 | DL |
| M3 | DL |
| M4 | DL |
| M5 | DL |

M6 (R85A) : Mutation of BLV NES

Figure 18 A and B
(A)
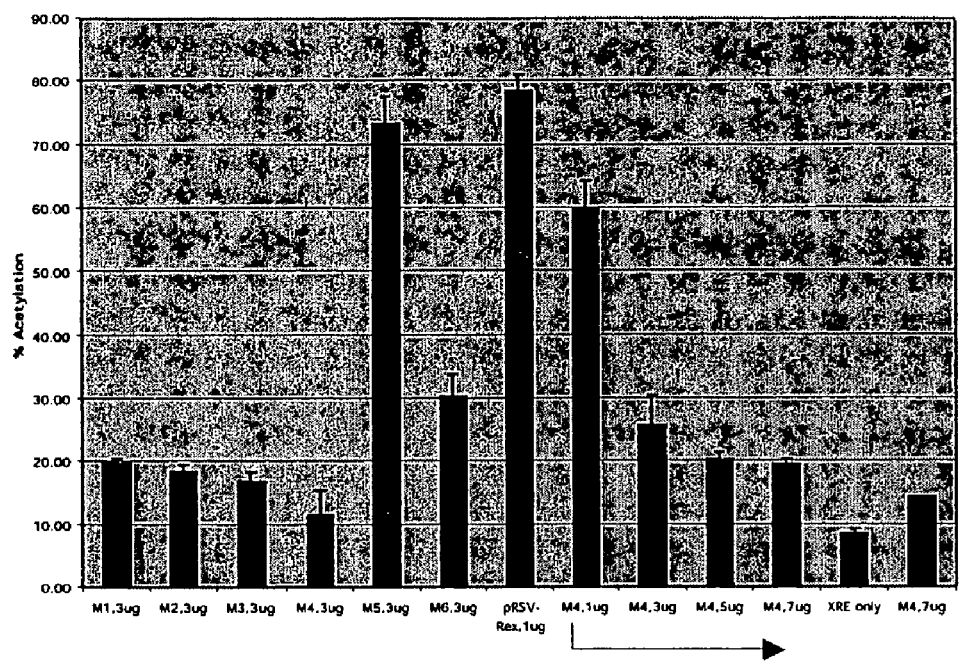
(B)
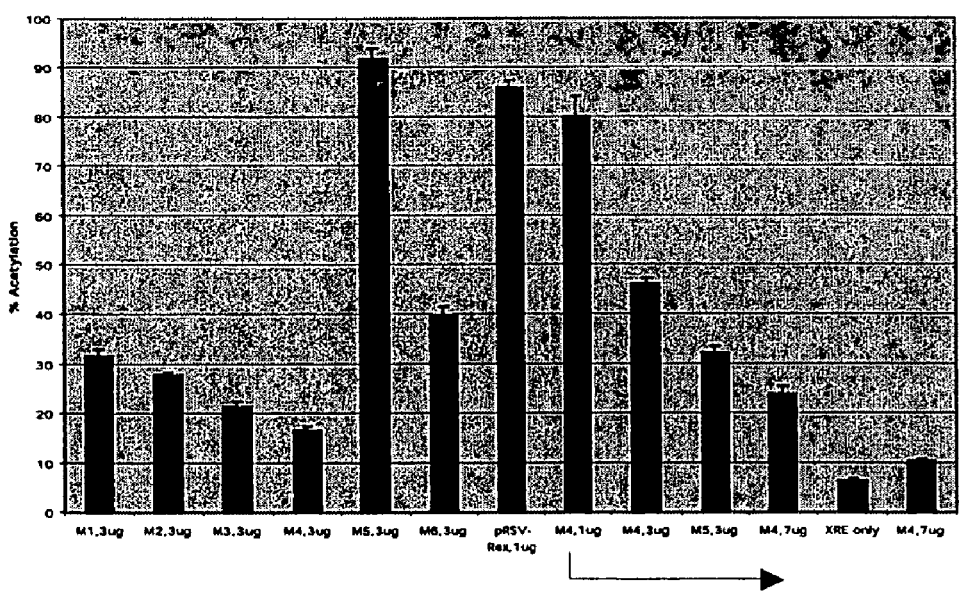

```
1   MPKERRSRRRPQ---PIIRWQVLLVGCPTLYMPARPWFCPMMSPSMPGAPSAGP  51
                                         M7  M8

52  MSDSNSKGSTPRSPARPTVSTGPPMDDLAASMERCSLDCMSPRPAPKGPDDSGSTAPFRP
    M9  M10                         M6

112 FALGPARFHFPPSSGPPSSPTNANCP  137
```

| | | |
|---|---|---|
| M1 | AAA | |
| M2 | DL | |
| M3 | DL | Double Mutant: Δ7/M4 |
| | | Δ2 : M2-M4 |
| M4 | DL | Δ3 : M3-M5 |
| | | Δ7 : M7-M8 |
| M5 | | DL |
| | | Δ8 : M8-M9 |
| M6 (R85A): Mutation of BLV NES | | Δ9 : M9-M10 |

SEQUENCE LISTING

<160> NUMBER OF SEQ ID NOS: 18

<210> SEQ ID NO 1
<211> LENGTH: 471
<212> TYPE: DNA
<213> ORGANISM: Bovine leukemia virus

<400> SEQUENCE: 1

```
atgcctaaaa aacgacggtc ccgaagacgc ccacaaccga tcatcagatg gcaagtgttg      60
ttggttgggg gccccactct ctacatgcct gcccggccct ggttttgtcc aatgatgtca     120
ccatcgatgc ctggtgcccc ctctgcgggc cccatgagcg actccaattc gaaaggatcg     180
acaccacgct cacctgcgag acccaccgta tcaactggac cgccgatgga cgaccttgcg     240
gcctcaatgg aacgttgttc cctcgactgc atgtctccga acccgcccc caagggcccc     300 gacgactctg gatcaactgc ccccttccgg ccgttcgcgc tcagcccggc ccggtttcac     360
tttccccctt cgagcggtcc cccttccagc cctaccaatg ccaattgccc tcggcctcta     420
gcgacggttg ccccattatc gggcacggcc ttcttccctg gaacaactta g              471
```

<210> SEQ ID NO 2
<211> LENGTH: 156
<212> TYPE: PRT
<213> ORGANISM: Bovine leukemia virus

<400> SEQUENCE: 2

```
Met Pro Lys Lys Arg Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Trp Phe Cys Pro Met Met Ser Pro Ser Met Pro Gly Ala Pro Ser
        35                  40                  45

Ala Gly Pro Met Ser Asp Ser Asn Ser Lys Gly Ser Thr Pro Arg Ser
    50                  55                  60

Pro Ala Arg Pro Thr Val Ser Thr Gly Pro Pro Met Asp Asp Leu Ala
65                  70                  75                  80

Ala Ser Met Glu Arg Cys Ser Leu Asp Cys Met Ser Pro Arg Pro Ala
                85                  90                  95

Pro Lys Gly Pro Asp Asp Ser Gly Ser Thr Ala Pro Phe Arg Pro Phe
            100                 105                 110

Ala Leu Ser Pro Ala Arg Phe His Phe Pro Pro Ser Ser Gly Pro Pro
        115                 120                 125

Ser Ser Pro Thr Asn Ala Asn Cys Pro Arg Pro Leu Ala Thr Val Ala
    130                 135                 140
```

```
Pro Leu Ser Gly Thr Ala Phe Phe Pro Gly Thr Thr
145                 150                 155
```

<210> SEQ ID NO 3
<211> LENGTH: 471
<212> TYPE: DNA
<213> ORGANISM: Bovine leukemia virus

<400> SEQUENCE: 3

```
atgcctaaaa aacgacggtc ccgaagacgc ccacaaccga tcatcagatg gcaagtgttg      60
ttggttgggg gccccactct ctacatgcct gcccggccca gatcttgtcc aatgatgtca     120
ccatcgatgc ctggtgcccc ctctgcgggc ccatgagcg actccaattc gaaaggatcg      180
acaccacgct cacctgcgag acccaccgta tcaactggac cgccgatgga cgaccttgcg     240
gcctcaatgg aacgttgttc cctcgactgc atgtctccga cccgccccc aagggcccc       300
gacgactctg gatcaactgc ccccttccgg ccgttcgcgc tcagcccggc ccggtttcac     360
tttcccctt cgagcggtcc cccttccagc cctaccaatg ccaattgccc tcggcctcta     420
gcgacggttg ccccattatc gggcacggcc ttcttccctg gaacaactta g              471
```

<210> SEQ ID NO 4
<211> LENGTH: 471
<212> TYPE: DNA
<213> ORGANISM: Bovine leukemia virus

<400> SEQUENCE: 4

```
atgcctaaaa aacgacggtc ccgaagacgc ccacaaccga tcatcagatg gcaagtgttg      60
ttggttgggg gccccactct ctacatgcct gcccggccct ggttttgtcc agatctgtca    120
ccatcgatgc ctggtgcccc ctctgcgggc ccatgagcg actccaattc gaaaggatcg      180
acaccacgct cacctgcgag acccaccgta tcaactggac cgccgatgga cgaccttgcg     240
gcctcaatgg aacgttgttc cctcgactgc atgtctccga cccgccccc aagggcccc       300
gacgactctg gatcaactgc ccccttccgg ccgttcgcgc tcagcccggc ccggtttcac     360
tttcccctt cgagcggtcc cccttccagc cctaccaatg ccaattgccc tcggcctcta     420
gcgacggttg ccccattatc gggcacggcc ttcttccctg gaacaactta g              471
```

<210> SEQ ID NO 5
<211> LENGTH: 471
<212> TYPE: DNA
<213> ORGANISM: Bovine leukemia virus

<400> SEQUENCE: 5

```
atgcctaaaa aacgacggtc ccgaagacgc ccacaaccga tcatcagatg gcaagtgttg      60
ttggttgggg gccccactct ctacatgcct gcccggccct ggttttgtcc aatgatgtca    120
ccatcgatgc ctggtgcccc ctctgcgggc ccatgagcg actccaattc gaaaggatcg      180
acaccacgct cacctgcgag acccaccgta tcaactggac cgccgatgga cgaccttgcg     240
gcctcaatgg aacgttgttc cctcgactgc atgtctccga cccgccccc aagggcccc       300
gacgactctg gatcaactgc ccccttccgg ccgttcgcgc tcagcccggc ccggttagat     360
cttcccctt cgagcggtcc cccttccagc cctaccaatg ccaattgccc tcggcctcta     420
gcgacggttg ccccattatc gggcacggcc ttcttccctg gaacaactta g              471
```

<210> SEQ ID NO 6
<211> LENGTH: 606

<212> TYPE: DNA
<213> ORGANISM: Bovine leukemia virus

<400> SEQUENCE: 6

```
atgcctaaaa aacgacggtc ccgaagacgc ccacaaccga tcatcagatg gcaagtgttg      60
ttggttgggg gccccactct ctacatgcct gcccggccca gatctgtcac catcgatgcc     120
tggtgccccc tctgcgggcc ccatgagcga ctccaattcg aaaggatcga caccacgctc     180
acctgcgaga cccaccgtat caactggacc gccgatggac gaccttgcgg cctcaatgga     240
acgttgttcc ctcgactgca tgtctccgag acccgccccc aagggccccg acgactctgg     300
atcaactgcc cccttccggc cgttcgcgct cagcccggcc cggttagatc ttccccttc     360
gagcggtccc ccttccagcc ctaccaatgc caattgccct cggcctctag cgacggttgc     420
cccattatcg ggcacggcct tcttccctgg aacaacttag taacgcatcc tgtcctcaga     480
aaagtcctta tattaaatca aatgggaccc cgaggggggg cccgaattcc ggatctttgt     540
gaaggaacct tacttctgtg gtgtgacata attggacaaa ctacctacag agatttaaag     600
ctctaa                                                                606
```

<210> SEQ ID NO 7
<211> LENGTH: 105
<212> TYPE: DNA
<213> ORGANISM: Bovine leukemia virus

<400> SEQUENCE: 7

```
atgcctaaag aacgacggtc ccgaagacgc ccacaaccga tcatcagatg gcaagtgttg      60
ttggttgggg gccccactct ctacatgcct gcccggccca gatct                     105
```

<210> SEQ ID NO 8
<211> LENGTH: 156
<212> TYPE: PRT
<213> ORGANISM: Bovine leukemia virus

<400> SEQUENCE: 8

```
Met Pro Lys Lys Arg Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Arg Ser Cys Pro Met Met Ser Pro Ser Met Pro Gly Ala Pro Ser
        35                  40                  45

Ala Gly Pro Met Ser Asp Ser Asn Ser Lys Gly Ser Thr Pro Arg Ser
    50                  55                  60

Pro Ala Arg Pro Thr Val Ser Thr Gly Pro Pro Met Asp Asp Leu Ala
65                  70                  75                  80

Ala Ser Met Glu Arg Cys Ser Leu Asp Cys Met Ser Pro Arg Pro Ala
                85                  90                  95

Pro Lys Gly Pro Asp Asp Ser Gly Ser Thr Ala Pro Phe Arg Pro Phe
            100                 105                 110

Ala Leu Ser Pro Ala Arg Phe His Phe Pro Ser Ser Gly Pro Pro
        115                 120                 125

Ser Ser Pro Thr Asn Ala Asn Cys Pro Arg Pro Leu Ala Thr Val Ala
    130                 135                 140

Pro Leu Ser Gly Thr Ala Phe Phe Pro Gly Thr Thr
145                 150                 155
```

<210> SEQ ID NO 9

```
<211> LENGTH: 156
<212> TYPE: PRT
<213> ORGANISM: Bovine leukemia virus

<400> SEQUENCE: 9

Met Pro Lys Lys Arg Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Trp Phe Cys Pro Asp Leu Ser Pro Ser Met Pro Gly Ala Pro Ser
        35                  40                  45

Ala Gly Pro Met Ser Asp Ser Asn Ser Lys Gly Ser Thr Pro Arg Ser
    50                  55                  60

Pro Ala Arg Pro Thr Val Ser Thr Gly Pro Pro Met Asp Asp Leu Ala
65                  70                  75                  80

Ala Ser Met Glu Arg Cys Ser Leu Asp Cys Met Ser Pro Arg Pro Ala
                85                  90                  95

Pro Lys Gly Pro Asp Asp Ser Gly Ser Thr Ala Pro Phe Arg Pro Phe
                100                 105                 110

Ala Leu Ser Pro Ala Arg Phe His Phe Pro Pro Ser Ser Gly Pro Pro
            115                 120                 125

Ser Ser Pro Thr Asn Ala Asn Cys Pro Arg Pro Leu Ala Thr Val Ala
        130                 135                 140

Pro Leu Ser Gly Thr Ala Phe Phe Pro Gly Thr Thr
145                 150                 155

<210> SEQ ID NO 10
<211> LENGTH: 156
<212> TYPE: PRT
<213> ORGANISM: Bovine leukemia virus

<400> SEQUENCE: 10

Met Pro Lys Lys Arg Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Trp Phe Cys Pro Met Met Ser Pro Ser Met Pro Gly Ala Pro Ser
        35                  40                  45

Ala Gly Pro Met Ser Asp Ser Asn Ser Lys Gly Ser Thr Pro Arg Ser
    50                  55                  60

Pro Ala Arg Pro Thr Val Ser Thr Gly Pro Pro Met Asp Asp Leu Ala
65                  70                  75                  80

Ala Ser Met Glu Arg Cys Ser Leu Asp Cys Met Ser Pro Arg Pro Ala
                85                  90                  95

Pro Lys Gly Pro Asp Asp Ser Gly Ser Thr Ala Pro Phe Arg Pro Phe
                100                 105                 110

Ala Leu Ser Pro Ala Arg Leu Asp Leu Pro Pro Ser Ser Gly Pro Pro
            115                 120                 125

Ser Ser Pro Thr Asn Ala Asn Cys Pro Arg Pro Leu Ala Thr Val Ala
        130                 135                 140

Pro Leu Ser Gly Thr Ala Phe Phe Pro Gly Thr Thr
145                 150                 155

<210> SEQ ID NO 11
<211> LENGTH: 201
<212> TYPE: PRT
<213> ORGANISM: Bovine leukemia virus
```

<400> SEQUENCE: 11

Met Pro Lys Lys Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Arg Ser Val Thr Ile Asp Ala Trp Cys Pro Leu Cys Gly Pro His
        35                  40                  45

Glu Arg Leu Gln Phe Glu Arg Ile Asp Thr Thr Leu Thr Cys Glu Thr
    50                  55                  60

His Arg Ile Asn Trp Thr Ala Asp Gly Arg Pro Cys Gly Leu Asn Gly
65                  70                  75                  80

Thr Leu Phe Pro Arg Leu His Val Ser Glu Thr Arg Pro Gln Gly Pro
                85                  90                  95

Arg Arg Leu Trp Ile Asn Cys Pro Leu Pro Ala Val Arg Ala Gln Pro
            100                 105                 110

Gly Pro Val Arg Ser Ser Pro Phe Glu Arg Ser Pro Phe Gln Pro Tyr
        115                 120                 125

Gln Cys Gln Leu Pro Ser Ala Ser Ser Asp Gly Cys Pro Ile Ile Gly
    130                 135                 140

His Gly Leu Leu Pro Trp Asn Asn Leu Val Thr His Pro Val Leu Arg
145                 150                 155                 160

Lys Val Leu Ile Leu Asn Gln Met Gly Pro Arg Gly Gly Ala Arg Ile
                165                 170                 175

Pro Asp Leu Cys Glu Gly Thr Leu Leu Leu Trp Cys Asp Ile Ile Gly
            180                 185                 190

Gln Thr Thr Tyr Arg Asp Leu Lys Leu
        195                 200

<210> SEQ ID NO 12
<211> LENGTH: 35
<212> TYPE: PRT
<213> ORGANISM: Bovine leukemia virus

<400> SEQUENCE: 12

Met Pro Lys Glu Arg Arg Ser Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Arg Ser
        35

<210> SEQ ID NO 13
<211> LENGTH: 133
<212> TYPE: PRT
<213> ORGANISM: Human T-cell leukemia virus

<400> SEQUENCE: 13

Met Pro Lys Thr Arg Arg Pro Arg Arg Ser Gln Arg Lys Arg Pro
1               5                   10                  15

Pro Thr Pro Trp Pro Thr Ser Gln Gly Leu Asp Arg Val Phe Phe Ser
            20                  25                  30

Asp Thr Gln Ser Thr Cys Leu Glu Thr Val Tyr Lys Ala Thr Gly Ala
        35                  40                  45

Pro Ser Leu Gly Asp Tyr Val Arg Pro Ala Tyr Ile Val Thr Pro Tyr
    50                  55                  60

```
Trp Pro Pro Val Gln Ser Ile Arg Ser Pro Gly Thr Pro Ser Met Asp
 65                  70                  75                  80

Ala Leu Ser Ala Gln Leu Tyr Ser Ser Leu Ser Leu Asp Ser Pro Pro
                 85                  90                  95

Ser Pro Pro Arg Glu Pro Leu Arg Pro Ser Arg Ser Leu Pro Arg Gln
            100                 105                 110

Ser Leu Ile Pro Gln Pro Pro Thr Phe His Pro Pro Ser Ser Arg Pro
        115                 120                 125

Cys Ala Asn Thr Pro
    130

<210> SEQ ID NO 14
<211> LENGTH: 480
<212> TYPE: DNA
<213> ORGANISM: Bovine leukemia virus

<400> SEQUENCE: 14
agatattgta tttaagtgcc tagctcgata caataaacgc catttgacca ttcaccacat      60
tggtgtgcac ctccaagctc caccgcggtg gcggccgctc tagaactagt ggatccccg     120 ggctgcagga attcgatcca catgcctaaa gaacgacggt cccgaagacg cccacaaccg    180
atcatcagat ggcaagtgtt gttggttggg ggccccactc tctacatgcc tgccccggccc   240 agatcttagt catggctaag atcttccccc ttcgagcggc cccccttcca gccctaccaa    300
tgccaattgc cctcggcctc tagcgacggt tgccccatta tcgggcacgg ccttcttccc    360
tggaacaact tagtaacgca tcctgtcctc agaaaagtcc ttatattaaa tcaaatggga    420
cctcgagggg gggcccgaat tccggatctt tgtgaaggaa ccttacttct gtggtgtgac    480

<210> SEQ ID NO 15
<211> LENGTH: 64
<212> TYPE: DNA
<213> ORGANISM: Artificial Sequence
<220> FEATURE:
<223> OTHER INFORMATION: Synthetic

<400> SEQUENCE: 15
ggggacaagt ttgtacaaaa aagcaggtct ccgccgccac catggcaagt gttgttggtt    60
gggg                                                                64

<210> SEQ ID NO 16
<211> LENGTH: 49
<212> TYPE: DNA
<213> ORGANISM: Artificial Sequence
<220> FEATURE:
<223> OTHER INFORMATION: Synthetic

<400> SEQUENCE: 16
ggggaccact ttgtacaaga aagctgggtc tcaaaaaagg cgggagagc                49

<210> SEQ ID NO 17
<211> LENGTH: 20
<212> TYPE: PRT
<213> ORGANISM: Human T-cell lymphotropic virus

<400> SEQUENCE: 17

Ser Leu Ile Gln Pro Pro Thr Phe His Pro Pro Ser Ser Arg Pro Cys
 1               5                  10                  15

Ala Asn Thr Pro
            20
```

-continued

```
<210> SEQ ID NO 18
<211> LENGTH: 26
<212> TYPE: PRT
<213> ORGANISM: Bovine leukemia virus

<400> SEQUENCE: 18

Phe Ala Leu Ser Pro Ala Arg Phe His Phe Pro Pro Ser Ser Gly Pro
1               5                   10                  15

Pro Ser Ser Pro Thr Asn Ala Asn Cys Pro
            20                  25
```

TRANSGENIC ANIMALS EXPRESSING TRANSDOMINANT NEGATIVE RETROVIRAL NUCLEIC ACIDS AND PROTEINS

This application claims priority to provisional patent application 60/442,047, filed Jan. 23, 2003, which is herein incorporated by reference in its entirety.

FIELD OF THE INVENTION

The present invention relates to compositions and methods for controlling complex retroviral infections. In particular, the present invention provides transgenic animals expressing a transdominant negative Rex gene product that inhibits retroviral replication and compositions for preventing retroviral replication.

BACKGROUND OF THE INVENTION

Bovine leukemia virus (BLV) is a retrovirus infection of dairy and beef cattle that causes malignant lymphoma. The clinical signs of BLV infection become evident as the tumors invade different tissues. Symptoms associated with BLV may include weight loss, decreased milk production, enlarged lymph nodes, loss of appetite, rear-limb weakness or paralysis, fever, protruding eyeballs, gastrointestinal obstruction, abnormal heartbeat, and abnormal blood lymphocyte count. Bovine malignant lymphoma (BML) may cause significant morbidity and mortality in some infected herds, especially when the prevalence of infection is high. BML usually is fatal because there are no drugs to treat this type of cancer.

Significant economic losses in domestic and international dairy and beef cattle herds occur each year as a consequence of BML. Additional economic losses resulting from BLV infection come from trade restrictions on infected animals and their germplasm.

In 1996 the National Animal Health Monitoring System (NAHMS), conducted by the U.S. Department of Agriculture-Animal and Plant Health Inspection Service-Veterinary Services (USDA-APHIS-VS), conducted an assessment of BLV prevalence in U.S. dairy herds. Between February and May of 1996, federal and state animal health officials contacted randomly selected dairy operations with at least 30 milk cows in 20 states, representing about 79 percent of the U.S. dairy cow population. Blood samples were collected from milk cows on 1007 participating operations and sent to the National Veterinary Services Laboratories for BLV testing using the agar gel immunodiffusion (AGID) test.

Results from this study indicated that 89 percent of all U.S. dairy operations harbored animals seropositive for BLV, while 43.5 percent of U.S. beef cattle operations harbored animals seropositive for BLV. BLV prevalence in the West, Midwest, and Northeast regions was between 87 to 89 percent. The operation prevalence in the Southeast region was 99 percent. BLV operational prevalence (94.7%) in herds with 200-plus cows was slightly higher than the prevalence in smaller operations. In the Southeast region, the individual-cow prevalence (68.8%) was much higher than in other regions. The individual-cow prevalence in operations with 200-plus cows (47.2%) was higher than the prevalence in smaller herds. The individual-cow prevalence was at least 25 percent on 7,546 of the positive operations.

Higher rates of infection are noted in larger herd units and in warmer climates. Transmission by biting insects is believed to be limited, but other practices in warm climates may amplify BLV (e.g., such as immunization against blood-borne infections like anaplasmosis and piroplasmosis using vaccines of blood origin). BLV infection among European dairy breeds in tropical countries is quite high. These milk-poor nations have even less economic incentive and capacity to attempt eradication of BLV than does the USA.

Parallels between the pathogenesis and epidemiology of BLV and Human T Cell Leukemia Virus 1 (HTLV-1) are beginning to be recognized. For example, the complex oncoviruses (e.g., BLV and HTLV-1) depend upon the function of Rex protein to mediate the export and expression of intron-containing viral RNAs encoding the Gag, Pol, and Env proteins needed for generating infection competent viral particles.

Despite an active retrovirus-specific cellular and humoral immune response, immune competent individuals fail to resolve infection early in the course of BLV, HTLV-1 and HTLV-2, and Human Immunodeficiency Virus (HIV) infections. (See, Piper, C. E., et al., Cancer Res., 35(10):2714-6 [1975]). BLV Virus apparently spreads because the immune response fails to eliminate infected cells, and in HTLV and HIV, a potent immune response does not correlate with slow progressor status (Pollari, F. L., et al., Can. J. Vet. Res., 56(4):289-95 [1992]). Activation and proliferation of cells, even immune cells, is required for proviral integration and retroviral replication. Thus, it appears that the mechanism responsible for the spread of BLV centers on immune responses that would activate infected B cells and prompt viral replication. When a BLV-infected animal responds to any antigen, bystander, provirus-carrying B cells at the site will be activated, triggering further BLV replication cycles and increasing the numbers of cells carrying integrated provirus. Thus, approaches to control BLV by enhancing the animal's immune response to the BLV virus are unlikely to succeed.

What is needed are compositions and methods for controlling the spread of BLV that are not based on conventional vaccinal or pharmacologic means.

SUMMARY OF THE INVENTION

The present invention relates to compositions and methods for controlling complex retroviral infections. In particular, the present invention provides transgenic animals expressing a transdominant negative retroviral (e.g., Rex) gene product that inhibits retroviral replication and compositions for preventing retroviral replication.

Without limiting the disclosed invention, in one preferred embodiment, the transgenic animals produced by the methods and compositions of the present invention are ungulates. In still further embodiments, the transgenic ungulates produced by the methods and compositions of the present invention are bovines.

The invention additionally provides transgenic animals that express transdominant negative retroviral processing proteins (e.g., TD BRex) which are integrated into animal breading programs. In this respect, the present invention contemplates transgenic animals (e.g., bovines) used to introduce genetic material into descendent transgenic animals. Accordingly, the present invention provides transgenic semen, oocytes, and embryos.

Also provided by the present invention are transdominant negative mutant Rex proteins that inhibit retroviral replication. In some embodiments, the transdominant negative mutant Rex proteins further comprise transdominant negative BLV Rex proteins. In still further embodiments, the transdominant negative mutant Rex proteins further comprise transdominant negative HTLV (i.e., HTLV-1 and HTLV-2) Rex proteins.

In some embodiments, the methods and compositions of the present invention provide nucleic acids that encode for transdominant negative retroviral proteins. In certain of these embodiments, the nucleic acids of the present invention encode for transdominant negative Rex proteins. In still further embodiments, the nucleic acids of the present invention encode transdominant negative BRex or HRex proteins. In preferred embodiments, the nucleic acids disclosed herein provide antiviral contracts that inhibit or control the spread of retroviruses (e.g., BLV and HTLV-1 or HTLV-2). The antiviral constructs disclosed herein are not intended to be limited any particular manner of nucleic acid composition. Indeed, the antiviral constructs of the present invention contemplate a number of different nucleic acid compositions comprising genes encoding transdominant negative retroviral proteins, including, but not limited to, plasmids, cosmids, bacterial artificial chromosomes, yeast artificial chromosomes, adeno-associated virus vectors, and adenovirus vectors. In addition to the nucleic acid sequences encoding for transdominant negative retroviral proteins and polypeptides disclosed herein, the antiviral constructs of the present invention may additionally comprise one or more additional nucleic acid sequences. In some embodiments, the antiviral constructs of the present invention may additionally comprise, for example, one or more nucleic acid sequences encoding promoters, enhancers, selectable markers, origin of replication, ribosome biding sites, and one or more sequences that encode cell surface proteins (e.g., antigens), etc. In still further embodiments, the present invention provides pseudotyped vectors expressing transdominant negative retroviral processing proteins (e.g., BRex and HRex).

In still other embodiments, the present invention provides transformed, transfected, or transduced host cells expressing transdominant negative retroviral proteins. For example, some embodiments of the present invention provide host cells that express transdominant negative mutant Rex proteins (e.g., TD BRex and TD HRex).

The invention further provides methods for preventing BLV infection in a cattle herd comprising: a) providing at least one transgenic bovine comprising a gene encoding a transdominant negative mutant of a Rex protein of BLV, and b) integrating offspring of said bovine into said cattle herd. In preferred methods of the preventing BLV infection in cattle herds, the transdominant negative mutation of the Rex gene encodes a gene product that inhibits BLV replication. In still other preferred methods of preventing BLV infection in cattle herds, the gene encoding a transdominant negative mutant of a Rex protein is inserted into a retroviral vector. In some of these embodiments, the retroviral vectors may further comprise nucleic acid sequences encoding one or more exogenous cell surface antigens (e.g., MHC class I antigen).

The present invention also provides methods for inhibiting infection by a retrovirus comprising: a) providing a subject at risk of retroviral infection and a vector encoding a transdominant negative mutant of a retroviral processing protein, and b) treating said subject with said vector under conditions such that said transdominant negative mutant of said retroviral processing protein is expressed and inhibits replication of said retrovirus. In certain embodiments, the vectors employed in the antiviral methods further comprise a vector encoding a transdominant negative mutant Rex protein selected from the group consisting of transdominant negative HRex and transdominant negative BRex. The methods of the present invention are not intended to be limited to any particular antiviral construct. Indeed, in some embodiments the methods disclosed herein employ retroviral vectors. In particularly preferred embodiments, the antiviral constructs comprise pseudotyped retroviral vectors.

DESCRIPTION OF THE FIGURES

FIG. 1A provides a drawing of pDM128 and pDM138 and various virus specific reporter constructs. FIG. 1B provides a gel showing induction of CAT activity by the addition of Rev-like proteins. FIG. 1C provides a gel showing that HBVPRE can stimulate localization of unspliced RNA to the cytoplasm.

FIG. 2 shows an alignment of the protein sequences of HRex (SEQ ID NO:13) and BRex (SEQ ID NO:9).

FIG. 3 provides a drawing showing an exemplary antiviral construct.

FIG. 4 provides a drawing showing an exemplary antiviral construct.

FIG. 5A provides a gel showing amplification of tax (691 bp) and mimic plasmids. FIG. 5B provides a graph showing the amplification of the DNA bands from FIG. 5A on a standard curve. FIG. 5C provides a gel showing amplification of pol (530 bp) and mimic plasmids. FIG. 5D provides a graph showing the amplification of the DNA bands from FIG. 5C on a standard curve.

FIG. 6 provides the nucleic acid sequence for Brex (SEQ ID NO:1).

FIG. 7 provides the amino acid sequence for Brex (SEQ ID NO:2).

FIG. 8 provides the nucleic acid sequence for mutant M7 (SEQ ID NO:3).

FIG. 9 provides the nucleic acid sequence for mutant M8 (SEQ ID NO:4).

FIG. 10 provides the nucleic acid sequence for mutant M4 (SEQ ID NO:5).

FIG. 11 provides the nucleic acid sequence for mutant M4Δ7 (SEQ ID NO:6).

FIG. 13 provides the amino acid sequence for mutant M7 (SEQ ID NO:8).

FIG. 14 provides the amino acid sequence for mutant M8 (SEQ ID NO:9).

FIG. 15 provides the amino acid sequence for mutant M4 (SEQ ID NO:10).

FIG. 16 provides the amino acid sequence for mutant M4Δ7 (SEQ ID NO:11).

FIG. 17 (SEQ ID NOS:17-18) provides a schematic depiction of the tested mutants.

FIGS. 18A and B provide a graphical comparison of the TD mutant activity of various mutants.

DEFINITIONS

Figure 12:
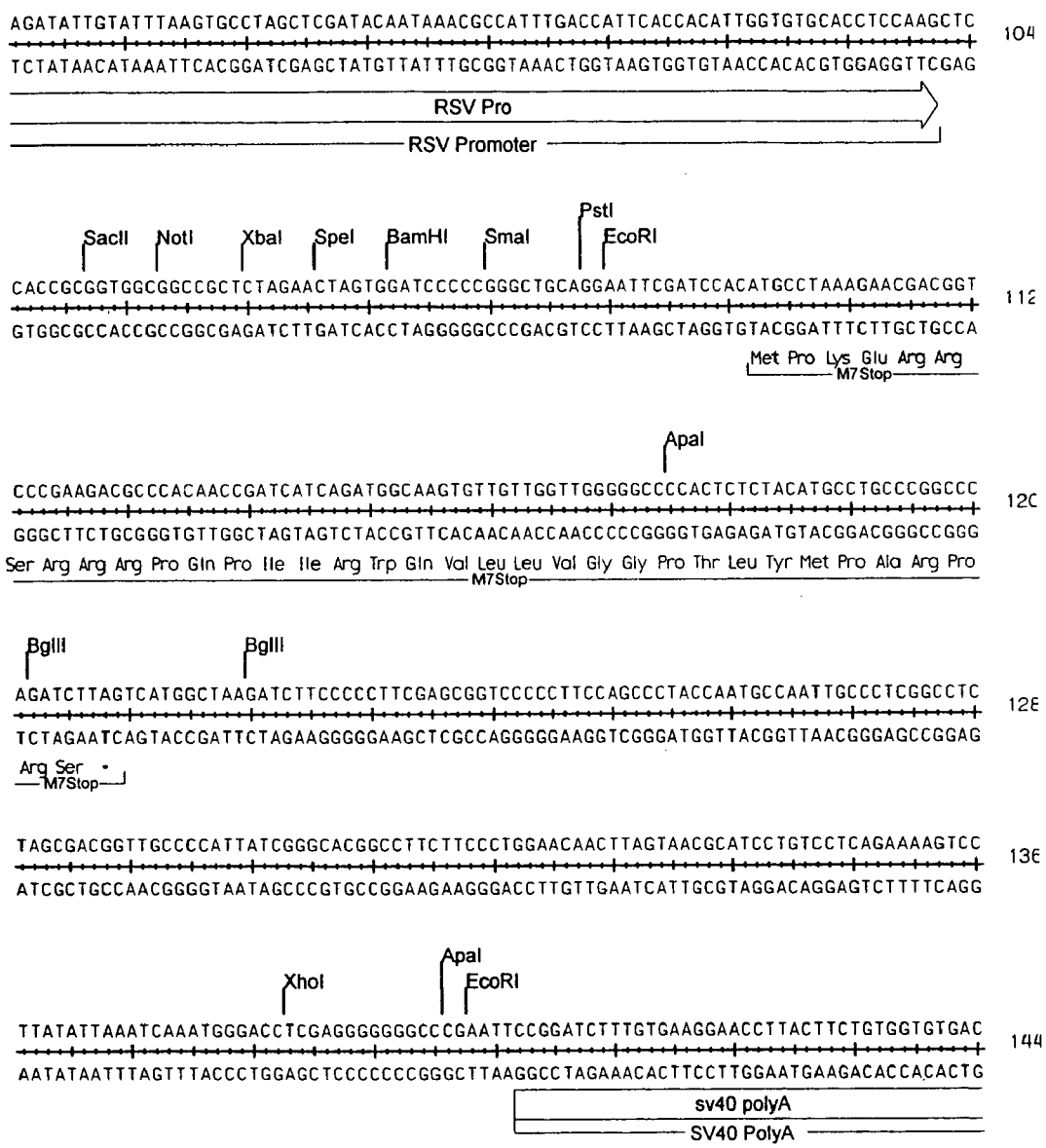
FIG. 12 provides the nucleic acid sequence for mutant M7stop (SEQ ID NO:7), the amino acid sequence for M7stop (SEQ ID NO:12), and the sequence for pRS (SEQ ID NO:14).
Figures 19, 20:
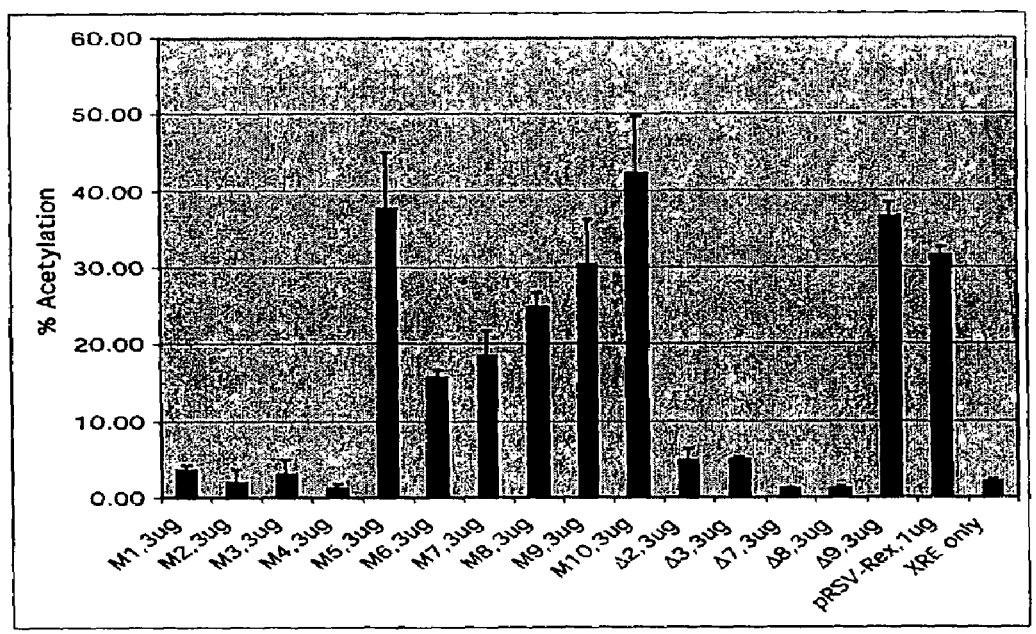
FIG. 19 (SEQ ID NO:9) provides a schematic depiction of the tested mutants.
FIG. 20 provides a graphical comparison of the TD mutant activity of various mutants.

To facilitate an understanding of the present invention, a number of terms and phrases are defined below:

As used herein, the term "host cell" refers to any eukaryotic cell (e.g., mammalian cells, avian cells, amphibian cells, plant cells, fish cells, and insect cells), whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors:host cells used during transfection or infection of host cells. For example, if 1,000,000 vectors are used to transfect 100,000 host cells, the multiplicity of infection is 10. The use of this term is not limited to events involving infection, but instead encompasses introduction of a vector into a host by methods such as lipofection, microinjection, calcium phosphate precipitation, and electroporation.

As used herein, the term "genome" refers to the genetic material (e.g., chromosomes) of an organism or a host cell.

The term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences, or portions thereof, of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "BLV rex gene" (or B rex) refers to the full-length BLV rex nucleotide sequence (e.g., contained in SEQ ID NO: 1). However, it is also intended that the term encompass fragments of the B rex sequence, as well as other domains within the full-length B rex nucleotide sequence. Furthermore, the terms "B rex nucleotide sequence" or "B rex polynucleotide sequence" encompasses DNA, cDNA, and RNA (e.g., mRNA) sequences. Similarly, the term "HTLV rex gene" (or H rex) refers to the full-length HTLV rex nucleotide sequence. However, it is also intended that the term encompass fragments of the H rex sequence, as well as other domains within the full-length H rex nucleotide sequence. Furthermore, the terms "H rex nucleotide sequence" or "H rex polynucleotide sequence" encompasses DNA, cDNA, and RNA (e.g., mRNA) sequences.

As used herein, the term "transdominant negative mutant Rex gene" refers to a Rex gene (e.g., SEQ ID NOs: 5 and 7) encoding a protein product (e.g., a transdominant negative mutant B rex or transdominant negative mutant H rex) that prevents other copies of the same gene, which have not been mutated (i.e., which have the wild-type sequence) from functioning properly.

As used herein, the term "exogenous gene" refers to a gene that is not naturally present in a host organism or cell, or is artificially introduced into a host organism or cell.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "protein of interest" refers to a protein encoded by a nucleic acid of interest.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain translated from the mRNA. The DNA or RNA sequence thus codes for the amino acid sequence.

As used herein, the term "native" (or wild type) when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

As used herein the term "retroviral processing protein" refers to a protein or polypeptide that functions to promote retroviral replication. Examples of retroviral processing proteins include, but are not limited to, BRex, HRex, and Rev proteins or functional polypeptides.

As used herein the term "transdominant rex mutant" (or TD rex mutant) refers to a nucleic acid sequence that encodes a protein or polypeptide that competes with or inhibits the function of a native Rex (wild type) protein or polypeptide. In particular, the terms "TD B rex," and "TD H rex," refer to nucleic acid sequences of BLV rex and HTLV rex that encode for TD BRex or TD HRex protein, respectively.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include, but are not limited to, the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp. 16.9-16.15.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1 gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue (e.g., cells infected with retrovirus, and more particularly, cells infected with BLV or HTLV). The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual*, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" or "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which is incorporated herein by reference) and woodchuck mRNA processing enhancer (WPRE; WO99/14310, incorporated herein by reference).

As used herein, the term "polycistronic" refers to an mRNA encoding more than polypeptide chain (See, e.g., WO 93/03143, WO 88/05486, and European Pat. No. 117058, all of which is incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements which allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein-coat) a heterologous nucleotide sequence, which in turn is flanked 5' and 3' by AAV ITRs. A number of techniques for constructing recombinant AAV virions are known in the art (See, e.g., U.S. Pat. No. 5,173,414; WO 92/01070; WO 93/03769; Lebkowski et al., Molec. Cell. Biol. 8:3988-3996 [1988]; Vincent et al., Vaccines 90 [1990] (Cold Spring Harbor Laboratory Press); Carter, Current Opinion in Biotechnology 3:533-539 [1992]; Muzyczka, Current Topics in Microbiol. and Immunol. 158:97-129 [1992]; Kotin, Human Gene Therapy 5:793-801 [1994]; Shelling and Smith, Gene Therapy 1:165-169 [1994]; and Zhou et al., J. Exp. Med. 179:1867-1875 [1994], all of which are incorporated herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See, e.g., Han et al., Proc. Natl. Acad. Sci. USA 88:4313-4317 [1991]; Uhlmann et al., Chem. Rev. 90:543-584 [1990]; Helene et al., Biochim. Biophys. Acta. 1049:99-125 [1990]; Agarwal et al., Proc. Natl. Acad. Sci. USA 85:7079-7083 [1989]; and Heikkila et al., Nature 328:445-449 [1987]). For a discussion of suitable ribozymes, see, e.g., Cech et al. (1992) J. Biol. Chem. 267:17479-17482 and U.S. Pat. No. 5,225,347, incorporated herein by reference.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known (See, e.g., Kotin, Human Gene Therapy 5:793-801 [1994]; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

DETAILED DESCRIPTION OF THE INVENTION

The present invention relates to compositions and methods for controlling complex retroviral infections. In particular, the present invention provides transgenic animals expressing a transdominant negative Rex gene product that inhibits retroviral replication and compositions for preventing retroviral replication.

In preferred embodiments, the methods and compositions of the present invention are used to produce transgenic animals that produce transdominant negative Rex gene products which inhibit the function of native Rex proteins in cells infected with complex retroviruses, especially, BLV or HTLV-1. In particularly preferred embodiments, the methods and compositions of the present invention are directed to producing transgenic ungulates (e.g., transgenic bovines) that are resistant to infection by BLV. The present invention is not intended to be limited, however, to the production of transgenic ungulates. Indeed, the present invention contemplates the production of a number of transgenic animal species that are resistant to infection by complex retroviruses.

The present invention also provides methods and compositions for the expression of transdominant rex equivalents in other retroviral species, such as the rev gene of HIV-1 virus in humans. These methods include the production of transgenic tissues, ex vivo, and human gene therapy.

Accordingly, the present invention provides methods and compositions for inhibiting the production of competent retroviruses, and more particularly, the production of competent complex oncoviruses, including BLV, HTLV-1 and HTLV-2. These methods and compositions are described in more detail below in the following sections: I) Overview of Rex Protein In Complex Retroviruses; II) Production of Transdominant Negative Rex Nucleic Acids And Gene Products; III) Approaches To Production of Transgenic Animals; and IV) Use in Gene Therapy.

I. Rex Protein In Complex Retroviruses

The present invention is not limited to a particular mechanism of action. Indeed, an understanding of the mechanism of action is not necessary to practice the present invention. Nevertheless, it is contemplated that functional Rex protein is required for the production of various complex retroviruses, including BLV and HTLV. Rex functions to mediate the export and expression of intron-containing viral RNAs encoding the Gag, Pol, and Env proteins which are needed to generate new retroviral particles. In preferred embodiments, the methods and compositions of the present invention are directed to inhibiting retroviral production (i.e., production of complex oncoviruses, and in particular BLV, HTLV-1 and HTLV-2). In particularly preferred embodiments, the methods and compositions of the present invention are directed to transgenic animals that produce transdominant negative derivatives of functional Rex proteins in cells and tissues (e.g., lymphocytes, and in particular B-lymphocytes) susceptible to complex retroviral infection.

A. Rex in BLV and HTLV

The BLV and HTLV-1 retroviral genomes both encode Rex proteins. These proteins are herein identified as BRex and HRex, respectively. Rex is a 27kD phosphorylated gene product that is critical for virus replication. Rex is derived from the X3' region of the genome and is encoded by the same doubly spliced mRNA as Tax. The rex gene encodes two proteins (27Da and 21kDa). The function of the smaller protein is unknown. The 27kDa Rex protein, unlike Tax, does not directly regulate transcription, but indirectly increases the expression of retroviral structural genes (i.e., gag and env) enzymatic genes (i.e., pol) by increasing transport of unspliced or singly spliced viral mRNA out of the nucleus into the cytoplasm of the infected cell. Once these mRNA transcripts enter the cytoplasm, expression of the structural proteins Gag and Env is initiated while expression of the regulatory proteins is concomitantly suppressed (See e.g., Hidaka, M., et al., EMBO J. 7:519 [1988]) or modulated (See e.g., Malim, M. H., et al., Nature, 335:181 [1988]). A doubly spliced mRNA transcript codes for the Rex protein itself, so as the concentration of Rex increases, it indirectly inhibits its own translation. This has implications with respect to the latency aspect of the HTLV virus.

Nuclear export of retroviral mRNA molecules occurs by the direct binding of Rex in a sequence specific region called the Rex Response Element (RexRE) in the 3' LTR of the molecule. The RexRE is a RNA stem-looped region that is highly stable and is present in all viral mRNA molecules. This means that another element is required in order to regulate expression and this element is called the cis-acting repressive sequence (CRS). When Rex binds the RexRE sequence it overcomes the inhibitory effect of the CRS. Since only unprocessed or singly spliced mRNA molecules contain both elements, only these elements are targeted for export to the cytoplasm and are consequently regulated by Rex activity. The RexRE is also known to have an activity apart from that of Rex, mainly RexRE aids in the 3' cleavage and polyadenylation of all HTLV-1 viral transcripts.

The ability of Rex to regulate expression of the BLV and HTLV-1 gag and env genes requires at least three functionally distinct activities: 1) nuclear and nucleolar localization (i.e., the capacity to be transported from the cytoplasmic site of synthesis of all proteins to the nucleus and there to be concentrated in the nucleolar region); 2) specific recognition (directly or indirectly) of the Rex responsive element sequence in viral RNAs; and 3) Rex effector activity. The Rex protein of HTLV-1 belongs to a family of proteins that use arginine-rich motifs (ARMs) to recognize their RNA targets.

Human Immunodeficiency Virus Type 1 (HIV-1) encodes a protein homologous to Rex known as Rev. Rev protein is like the Rex in that it is required for the expression of viral structural proteins and thus production of competent viruses. In HIV-1, the selectivity of the induction noted above is due to an RNA target sequence required for Rev function termed Rev Response Element (RRE). RRE coincides with a large, 234 nucleotide RNA secondary structure present within the HIV-1 env gene.

The importance of Rex and Rev in the replication of complex retroviruses, respectively, is underscored by the fact that in spite of having different primary structures, Rex and Rev proteins are functionally related. For example, it is possible to substitute functional HTLV-1 Rex for defective Rev in the HIV-1 system, moreover, it has recently been found that HTLV-1 Rex and HIV-1 Rev can substitute for HIV-2 Rev (Rev2) and that HTLV-1 Rex can also substitute for the analogous HTLV-2 regulatory protein. (See e.g., Rimsky, L., et al., Nature, 335:738 [1988]). This complementation is sufficient to rescue rev-deficient HIV-1 provirus by providing functional Rex protein in trans. On the other hand, attempts to rescue a rex-deficient HTLV-1 provirus by addition of a functional Rev protein have been unsuccessful. This lack of reciprocation is not fully understood, but it probably relates to differences in the functional aspects of these proteins required for target RNA sequence recognition.

B. Similarities between BLV and HTLV Infection

Parallels exist between the pathogenesis and epidemiology of BLV and HTLV-1 (See e.g., Burny A., et al., Retrovirus Biology and Human Disease., Eds. Gallo, R., and Wong-Staal, F., Dekker, New York, N.Y., p. 9 [1990]). Human T-cell leukemia virus types 1 and 2 (HTLV-1 and HTLV-2) are complex oncogenic retroviruses that transform primary human T cells in culture and are associated with leukemia and neurological disorders in humans. (See e.g., Gree, P. L., et al., The Retroviridae, p. 227-311, vol. 3, Eds. Levy, J. A., Plenum Press, New York, N.Y., [1994]). Preferred embodiments of the methods and compositions disclosed herein provide an innovative approach to controlling BLV infection in cattle populations and for developing animal and population models for studying methods for controlling HTLV infection in humans, as well as methods of controlling other complex oncoviruses.

As indicated above, BLV shares many common features with HTLV-1, making BLV infected animals an excellent animal model for testing therapies to combat HTLV infection. For example, BLV and HTLV-1 both have: 1) similar genetic organizations; 2) an early polyclonal phase of infection (See e.g., Ghysdael, K., et al., Current Topics in Microbiology and Immunology 112:1 [1984]); 3) a monoclonal or oligoclonal tumor phase; 4) provirus integration but lack of viremia in tumor cells (Orlik, O., and Splitter G. A., J. Virol., 70(11):7584 [1996]); and 5) spontaneous proliferation of lymphocytes in vitro with retrovirus production (Elovaara, I., et al., J. Exp. Med., 177:1567 [1993]). In BLV, this phenomenon is dependent on CD4+ T cells, while in HTLV-I, CD8+ T cells contribute to spontaneous lymphocyte proliferation (Lassauzet, M L, et al., Amer. J. Epidemiol, 133:164-76 [1991]. Common to both BLV and HTLV-I are: 1) long-term retroviral antigen production (Lassauzet, M. L., et al., Can. J. Vet. Res. 54:184-189 [1990]); 2) continual retroviral specific immune stimulation demonstrated by persistent BLV and HTLV antibody production indicating continuing antigen stimulation (Burny A., et al., Retrovirus Biology and Human Disease., Eds. Gallo, R., and Wong-Staal, F., Dekker, New York, N.Y., p. 9 [1990]); and 3) T cell proliferation to virtually all BLV proteins (Elovaara I., et al., J. Exp. Med., 177:1567 [1993]) and cytotoxic T cells to envelope proteins and CD8 CTL in HTLV-1. For both BLV and HTLV transmission is effected by minute doses of blood, and less commonly milk or saliva, transferred from infected to susceptible individuals (Buxton, B. A., and Schultz, R. D., Can. J. Comp. Med., 48(4):365-369 [1984]).

In some preferred embodiments of the present invention, methods and compositions are disclosed for the retrovector-based gene transfer of BLV resistance into a very small portion (less than about 3%) of a bovine population selected to become parents of each new generation of bulls in controlled bovine breading programs. For instance, one or more transgenic bovines capable of expressing transdominant negative BRex may are raised to sexual maturity and their gametic cells are introduced into bovine breading programs. In some embodiments, the transdominant negative bovines raised for this purpose are female bovines, likewise, in other embodiments, the bovines are male. The efficiency of this technologies described herein allow for preservation of non-transgenic full-sibs to the transgenic animals, important to both theoretical genetic diversity and to acceptance in parts of the world where BLV has been controlled by traditional means. This provides a tool for long term comparative evaluation of the efficacy of the disclosed anti-BLV therapies in a bovine population. Ongoing evaluating the various methods and compositions disclosed herein in controlling BLV in naturally infected bovine herds over time lends itself to robust statistical inference.

It is expected that demonstration of the in vivo efficacy of the TD BRex genes in controlling BLV in bovine herds will provide guidance for the development of gene therapy tools for controlling HTLV.

One aspect of the present invention involves inhibiting or overproducing deleterious gene products by manipulating the gene encoding these products thus creating dominant negative mutations that encode mutant retroviral regulatory proteins which when expressed disrupt the activity of wild-type proteins. In the situation of viral, especially retroviral, infections it is highly desirable to provide corresponding transdominant repressors of virus function by the construction of similar inhibitors of essential regulatory genes, e.g., inhibitors of the rex or rev genes. Accordingly, the present invention provides compositions and methods for expressing transdominant negative mutations of retroviral proteins (e.g., structural, enzymatic, etc.) in a host cell. In particularly preferred embodiments of the present-invention compositions and methods are provided for expressing transdominant negative mutations of the Rex retroviral protein.

II. Production of Transdominant Negative Rex Nucleic Acids and Gene Products

A. Generation of Dominant Negative Rex Proteins

The Rex gene may be recovered from any isolate of BLV or HTLV (i.e., HTLV-1 or HTLV-2). The Rev gene may be recovered from any isolate of HIV-1, while pgTAX-LTR may be recovered, for example, from HUT102 or MT1. In particular, the Rex coding sequence may be obtained as described in Rimsky, L., et al., Nature, 335(6192):738-40 [1988]) from the plasmid pcRex (=pRex). The rex gene may be cloned in a manner analogous to that previously described for the gag, pol, env, and tax genes of HTLV-1 from the whole genome of established HTLV-1 in infected cell lines such as HUT102 (TIB 162) and MT2 by using, for example, the polymerase chain reaction. (See e.g., De, B. K., and Srinivasan, A., Nucl. Acid Res., 17(5):2142 [1989]). Numerous sources of wild-type HTLV virus genome are known in the art, for example, GenBank Accession Nos.: M10085, M37302, J02029, AF139170, and M69044 provide wild-type HTLV sequences from which Rex coding sequences can be isolated as described in Rimsky, infra.

Rex and Rev coding sequences may also be synthesized, and thus rationally altered, by techniques well known in the art for the chemical synthesis of nucleic acid molecules. Thus, in some embodiments, a transdominant repressor of Rex or Rev function is made by standard recombinant DNA methods or by standard chemical methods of peptide synthesis, or by a combination of these conventional methods. In some embodiments, a transdominant repressor of Rex protein function is produced that is also capable of repressing the function of the structurally unrelated, but functionally equivalent, Rev protein in HIV-1 and HIV-2.

In still further embodiments, a wild-type rex nucleic acid sequence can be mutated using one of a variety of commercially available mutagenesis kits. In this regard, the present invention contemplates, for example, that the GENEEDITIOR system, Promega, Madison, Wis., covered under U.S. Pat. No. 5,780,270, or the SCULPTOR mutagenesis system, Amersham Pharmacia Biotech, Piscataway, N.J., as described in Taylor, J. W., et al., *Nucl. Acids Res.*, 13:8764 (1985); Nakamaye, K., and Eckstein, F., *Nucl. Acids Res.*, 14:9679 (1986), can be used create transdominant negative rex mutations.

Studies of HRex have identified two regions of the protein that when disrupted generate transdominant negative derivatives (See, FIG. 2, amino acids 58-66 and 119-122). Accordingly, while not being limited to alterations in these regions of the Rex amino acid sequence, in preferred embodiments development of dominant negative derivatives of BRex are directed to altering the rex nucleic acid sequence that encodes for the amino acids with these defined regions. FIG. 2 shows an alignment of the protein sequences of Hrex (SEQ ID NO:13) and Brex (SEQ ID NO:2). The bolded amino acids in FIG. 2 show the alignment of the nuclear export signals (NES) of BRex and HRex. Significant regions of conservation appear in the amino-terminal regions encompassing the nuclear localization and RNA binding domains and amino acids 117-128 of BRex, which overlaps with a region sensitive to dominant negative mutations previously defined in HRex.

Based on the similarity between BRex and HRex shown in FIG. 2, the mutant designated BRex M4 was generated (SEQ ID NO:5). The efficacy of potential transdominant negative mutants can be assayed as described herein and the best transdominant mutants selected for further use. Exemplary assays for the determination of transdominant negative mutant function include the RNA Export Assay (Example 1) and the Bat Lung Cell Assay. For example, the RNA Export Assay is used to determine if the BRex M1 mutation disrupts BRex function. In this assay, a specific reporter for BRex is made by inserting a fragment encompassing the BLV Rex responsive element into plasmid pDM128 in place of the rev-responsive element for HIV-1. The reporter plasmid and increasing amounts of the putative TD BRex expression plasmid are then co-transfected with a constant amount of the wild type expression plasmid in a dose response study. If the mutated derivative of BRex is dominant negative, a concentration dependent decrease in BRex function as detected by the BRex reporter will be observed.

Accordingly, the present invention provides nucleic acid and amino acid sequences and variants and homologs thereof encoding transdominant negative mutants of the wild-type BLV Rex protein. Exemplary TD BRex nucleic sequences include, but are not limited to, SEQ ID NOs: 5 and 7. Exemplary TD BRex amino acid sequences include, but are not limited to, SEQ ID NOs: 9 and 11. The present invention is not limited to these particular sequences. Indeed, in some preferred embodiments, the present invention provides homologous nucleic acid sequences encoding TD BRex mutants that hybridize to SEQ ID NOs:5 and 6 under conditions of high to low stringency. In other preferred embodiments, the present invention provides homologous nucleic acid sequences encoding the amino acid sequences of SEQ ID NOs:5 and 7. It is contemplated that the nucleic acid sequences may encode proteins of shorter length than the full-length wild-type sequence (e.g., SEQ ID NO:7). In preferred embodiments, the full-length and truncated sequences encode a transdominant negative protein that inhibits the function of Rex, and more particularly BRex. It will be understood that the truncated sequences are not limited to the length of SEQ ID NO:7. Indeed, additional amino acids may be added to or deleted from this sequence. TD mutant resulting from such isolations and deletions, as well as substitution mutations are conveniently identified by the assays described herein.

B. Effects of Transdominant Negative Mutations

Mutations in retroviral regulatory proteins (e.g., Rex or Rev) can yield gene products with a dominant negative phenotype over the wild-type function (See e.g., Herskowitz, I., Nature 329:317 [1987]). Dominant negative mutant proteins, known as trans-dominant repressors, represent a novel class of potential anti-viral agents. In genetic analyses, negative mutations are those that cause a diminution or loss of a function of a gene. Dominant negative mutations are those that prevent other copies of the same gene, which have not been mutated (i.e., which have the wild-type sequence) from functioning properly. On the other hand recessive negative mutations do not so inhibit wild-type counterparts. Further, some dominant mutations inhibit wild-type genes only when the mutant and wild-type genes are located on the same chromosome (DNA or RNA molecule). In this case the inhibiting mutation is said to be "cis-acting". Alternatively, a dominant mutation may inhibit the corresponding wild-type gene even when located on a separate chromosome. This type is classified as a "trans-acting" dominant mutation or, more simply, as a transdominant mutation.

Several transdominant genes for eukaryotic or Herpes virus transcription factors (See e.g., Hope, I. A., and Struhl, K., Cell 46:885 [1986]; Gentz, R., et al., Science 243:1695 [1989]; Triezenberg, S. J., et al., Gen. & Devel., 2:718 [1988]; Friedman A. D., et al., Nature, 335:452 [1988]) have been described. For example, when overexpressed some deletion mutants of the Herpes simplex virus trans-activator VP16 inhibit VP16 function, thereby preventing replication of HSV-1 in normally permissive cells. In regard to retroviruses, several transdominant retroviral mutants have been described, for example, transdominant mutants of the HTLV-II tax (See e.g., V. Wachsman, V., et al., Science 235:674 [1987]) and HIV-1 tat (See e.g., Green, M., et al., Cell 58:215 [1989]) and gag proteins (See e.g., Trono, D., et al., Cell 59:113 [1989]). In particular, transdominant negative derivatives of HTLV-1 have been identified. (See e.g., Orlik, O., and Splitter G. A., J. Immunol. Methods 199:159 [1996]). These derivatives likely inhibit Rex function through the formation of non-functional multimers. Similar transdominant negative derivatives of the HIV Rev are in clinical trials, indicating the potential for this type of intracellular antiviral therapy. (See e.g., Kimata, J. J., et al., J. Virol., 67:3134 [1993]). Transdominant negative mutations of the Rex protein have also been described in the patent literature, for example, U.S. Pat. Nos. 5,871,958, and 6,162,898, and EP 0406557, each of which is herein incorporated by reference in its entirety.

C. Construction of Antiretroviral Constructs

Some embodiments of the present invention provide methods and compositions comprising a single gene vector construct encoding TD BRex (or TD HRex) protein. The present invention is not limited to any particular vector. Indeed, the use of a variety of vectors is contemplated, including, but not limited to plasmids, cosmids, bacterial artificial chomosomes, yeast artificial chromosomes, adeno-associated virus vectors, and adenovirus vectors. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In some preferred embodiments, the vector is a retroviral vector. Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products) which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (–PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes which are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles which lack a membrane-associated protein (e.g., an env protein). In order to produce viral particles containing a membrane associated protein which will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles which contain the membrane-associated protein expressed by the transfected packaging cell line; these viral particles which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or ape), and the thymidine kinase promoter.

In other embodiments of the present invention, where secretion of the protein of interest is desired, the vectors are modified by including a signal peptide sequence in operable association with the protein of interest. The sequences of several suitable signal peptides are known to those in the art, including, but not limited to, those derived from tissue plasminogen activator, human growth hormone, lactoferrin, alpha-casein, and alpha-lactalbumin.

In other embodiments of the present invention, the vectors are modified by incorporating an RNA export element (See, e.g., U.S. Pat. Nos. 5,914,267; 6,136,597; and 5,686,120; and WO99/143 10, all of which are incorporated herein by reference) either 3' or 5' to the nucleic acid sequence encoding the protein of interest. It is contemplated that the use of RNA export elements allows high levels of expression of the protein of interest without incorporating splice signals or introns in the nucleic acid sequence encoding the protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. In some embodiments, the selectable marker gene is provided as part of polycistronic sequence that also encodes the protein of interest.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

The low titer and inefficient infection of certain cell types by MoMLV-based vectors has been overcome by the use of pseudotyped retroviral vectors that contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the Vesiculovirus genera other than VSV, such as the Piry and Chandipura viruses, that are highly homologous to the VSV G protein and, like the VSV G protein, contain covalently linked palmitic acid (Brun et al. Intervirol. 38:274 [1995] and Masters et al., Virol. 171:285 (1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein as described in Example 2, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses which have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

For example, in one such embodiment, the construct backbone comprises: 1) the Murine Sarcoma Virus 5' LTR; 2) extended viral packaging signal (ψ); 3) a selectable marker (e.g., neo); 4) an internal promoter with an appropriate cloning site (e.g., the native BLV U3 promoter); and 5) the 3' Murine Leukemia Virus 3' LTR. In some embodiments, in some embodiments of the present invention a post-transcriptional enhancer element is added to the retrovector backbone construct in order to optimize the transport of the message from the nucleus to the cytoplasm. In certain of these embodiments, the vector additionally comprises a RNA transport signal (e.g., from woodchuck hepadna virus, WPRE). The Woodchuck hepadna virus post transcriptional enhancer is contemplated to enhance the cytoplasmic levels of RNA and to enhance the translation of the target protein. Tests with retrovector backbone constructs comprising Woodchuck hepadna virus post transcriptional enhancer increase the titer of the MLV-based vectors (presumably by increasing the viral genome transport) and increases the expression of intron-less messages. In particularly preferred embodiments, the Woodchuck hepadna virus post transcriptional enhancer element is inserted in the 3'UTR region of the vector where the remainder of the 3'UTR region is contributed by MLV. FIG. 3 presents a diagrammatic representation (not to scale) of a possible retrovector backbone construct contemplated by the present invention under the above described scheme (i.e., depicting an optional RNA transport signal).

Still other embodiments of the present invention provide methods and compositions for the expression of a cell surface antigen to attract cell mediated cytotoxic immunity to eliminate infected cells (TD Rex-CS constructs) in addition to expression of transdominant negative Rex gene products. While not limited to any particular mechanism or understanding of the antiviral effects achieved by the present invention, some antiviral vectors additionally comprise one or more nucleic acid sequences encoding for one or more cell surface antigens. Such embodiments are contemplated to provide added antiviral benefits in view of the fact that retroviruses have a dual mechanism of replication and survival (i.e., viral replication and by replication of cells containing proviruses).

In some instances, the antiviral benefits of the basic constructs disclosed herein may provide only partial retroviral inhibition in infected cells. For example, if the timing or the quantity of TD Rex expression is insufficient, some "leakage" could occur leading to a low level of viral replication. This may result in lower titers of virus in the host's blood and possibly a slow rate of transmission in a susceptible population. As such, it is a further aspect of the present invention to provide additional methods and compositions to mitigate this possibility mechanism of infection. Since expression of Rex occurs after the integration of proviral DNA, inducing destruction of the infected cell by cell mediated cytotoxic immunity will eliminate proviral particles and potential carrier cells.

In order to overcome the possible "leakiness" if Rex inhibition of viral replication is not complete, the present invention contemplates a second set of vectors constructed from TD BRex and TD HRex. In preferred embodiments, these vectors are similar follow to the constructs outlined above, but encode an additional gene coding for a selected cell surface antigen. A desired characteristic of this epitope would be that it generates a strong cell mediated immune response. In some embodiments, the constructs disclosed herein encode the murine MHC class I antigen. The present invention, however, when describing constructs encoding cell surface antigens (i.e., TD Rex-CS constructs) is not limited to employment of murine MHC class I antigen, indeed, various strong effectors of cell mediated cytotoxic immunity could be expressed in the particular host cells.

In those embodiments which comprise nucleic acid sequences encoding for a cell surface antigen (e.g., MHC) a wide array of analytical tools and procedures for cell selection, sorting, and in vitro analytical procedures are known in the art.

Preferred embodiments of the bicistronic vectors (TD Rex-CS constructs) comprise an IRES-linked gene for the MHC epitope. Similar bicistronic vectors to express light and heavy chains of antibodies in stochiometric proportions have been described. In some preferred embodiments of TD Rex-CS constructs, the standard backbone is as follows: 1) the Murine Sarcoma Virus 5' LTR; 2) extended viral packaging signal (ψ); 3) selectable marker; 4) an internal promoter with an appropriate cloning site; 5) an optional internal ribosome entry site (IRES); 6) a cell surface marker (e.g., epitope from murine MHC class I surface marker; CSM); 7) a RNA transport signal (e.g., from woodchuck hepadna virus) (WPRE); 8) the 3' Murine Leukemia Virus 3' LTR. Those skilled in the art will readily appreciate that other backbone schemes are possible and would require no more than routine molecular manipulation to construct. In the preferred scheme for TD Rex-CS constructs described above, the constructs may or may not comprise an a RNA transport signal, and are not intended to be limited to encoding murine MHC class I surface marker.

Methods and sources for the cDNA encoding the murine MHC class I antigen, or other cell surface antigens that prompt a strong cell mediated cytotoxic response in a particular host cell, are known in the art and can be incorporated into the antiviral vectors disclosed herein using standard molecular biology techniques. DNA sequencing can be performed on all of the gene constructs to confirm that no mutations were introduced during the cloning and that the coding sequences are as predicted.

In still further embodiments, the methods and compositions of the present invention provide bicistronic vectors that also display green fluorescent protein (GFP) as a means for identifying and sorting infected cells expressing Rex protein. It is contemplated that these particular constructs will be used as in vitro tools to confirm infection and function of the Rex protein in cell lines.

The present invention also contemplates the use of lentiviral vectors to generate high copy number cell lines. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

III. Production of Transgenic Animals

The present invention contemplates the generation of transgenic animals comprising an exogenous transdominant negative Rex (i.e., TD BRex or TD HRex) gene or homologs, mutants, or variants thereof. In preferred embodiments, the constructs of the present invention are used to create transgenic cell lines and animals, in particular transgenic ungulates, and more particularly transgenic bovine. A variety of methods are known for creating transgenic cell lines and animals.

In preferred embodiments, the transgenic animal displays an altered phenotype as compared to wild-type animals. In preferred embodiments, the altered phenotype is the over-expression of mRNA for a TD Rex gene as compared to wild-type levels of Rex expression in cell infected with complex retrovirus (i.e., BLV, or HTLV-1 and HTLV-2). Methods for analyzing the presence or absence of such phenotypes include Northern blotting, mRNA protection assays, and RT-PCR. The transgenic animals of the present invention find use as models for testing retroviral therapies, and more generally as systems for research into the biology and pathology of complex retroviruses.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1-2 picoliters (p1) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoel (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In particularly preferred embodiments, the transgenic animals, and in particular transgenic bovines, are created using a vesicular stomatitis virus (VSV) envelope protein pseudotyped replication defective retroviral gene delivery vector as by the method described in Chan A. W. S., et al., Proc. Natl. Acad. Sci. USA, 95:14028 (1998).

Briefly, most retroviruses only infect dividing cells, because of a critical need for nuclear membrane breakdown to allow the pre-integration complex to contact the chromosomal DNA. The nuclear membrane breakdown that occurs in the oocyte, during metaphase II (MII) of the second meiosis, provides a window during which integration can readily occur. The method described in Chan et al., (gene introduction by injection into the perivitelline space of the acolytes during metaphase II arrest) followed by in vitro fertilization and embryo transfer, provides that nearly 100% of the offspring born will be transgenic heterozygotes.

The approach to transgene insertion described by Chan et al., overcomes four major problems in the more traditional forms of transgenic production currently in use, such as, pronuclear microinjection and nuclear transfer: 1) efficiency of transgenic live births achieved is a hundred-fold higher that of other methods; 2) genes insert as single copies, with less risk of genetic instability upon subsequent cell replication; 3) transgenes are inserted prior to fertilization, eliminating mosaicism; and 4) animals (i.e., bovine calves) undergo normal gestation and birth. On-going evaluation of second generation transgenic animals (i.e., bovine) produced by the Chan et al., method show Mendelian inheritance and gene stability.

IV. Gene Therapy Using Transdominant Negative Mutations of Rex

The present invention also provides methods and compositions suitable for gene therapy to alter Rex expression, production, or function in cell infected with complex retroviruses. As described above, the present invention provides HTLV and BLV genes and provides methods of obtaining rex genes from other complex retroviruses. Thus, the methods described below are generally applicable across many species susceptible to infection by complex retroviruses.

Viral vectors commonly used for in vivo or ex vivo targeting and gene therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be targeted. Examples of particular vectors include, but are not limited to, a defective herpes virus 1 (HSV1) vector (See e.g., Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12) or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. While the present invention is not intended to be limited to any particular serotypes, type 2 or type 5 human adenoviruses (Ad 2 or Ad 5), or adenoviruses of animal origin (See e.g., WO94/26914) are specifically contemplated by the present invention. Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al, J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell, 33:153 [1983]; Markowitz et al., J. Virol., 62:1120 [1988]; PCT/US95/14575; EP 453242; EP178220; Bernstein et al, Genet. Eng., 7:235 [1985]; McCormick, BioTechnol., 3:689 [1985]; WO 95/07358; and Kuo et al., Blood, 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963-967 [1992]; Wu and Wu, J. Biol. Chem., 263:14621-14624 [1988]; and Williams et al., Proc. Natl. Acad. Sci. USA 88:2726-2730 [1991]). Receptor-mediated DNA delivery approaches can also be used (Curiel et al., Hum. Gene Ther., 3:147-154 [1992]; and Wu and Wu, J. Biol. Chem., 262: 4429-4432 [1987]).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); cm (centimeters); mm (millimeters); µm (micrometers); nm (nanometers); and C (degrees Centigrade).

Example 1

Development of A Rapid and Quantative Assay for RNA Export

This example describes experiments to study retroviral RNA export using a highly sensitive and versatile transient co-transfection assay system based on a reporter plasmid (pDM128) derived from the env region of HIV-1. (See e.g., Hope T. J., et al. Proc. Natl. Acad. Sci. USA, 87:7787-91 [1990]). The transcript produced by pDM128 includes a single large intron containing both the Rev-responsive element (RRE) and the chloramphenicol acetyltransferase (CAT) coding sequence. The CAT coding sequence is excised when the RNA is spliced. Cells transfected with pDM128 alone express very little CAT activity; co-transfection of pDM128 with a functional Rev expression plasmid, however, permits the unspliced transcripts of pDM128 to enter the cytoplasm, and strongly induce CAT expression. The specificity of this assay can be changed by the insertion of specific response elements identified in other viral systems. Heterologous response elements are inserted into the reporter pDM138 (Huang X., et al., J. Virol., 65:2131-2134 [1991]) which was derived from pDM128 by the deletion of 1.2 kb of the HIV-1 encompassing the RRE and the subsequent insertion of a unique restriction enzyme at the site of the deletion. The generation ofpDM138 and its use to study the regulated export of unspliced mRNA is diagrammed in FIG. 1 that shows various species-specific reporters for facilitated and nuclear export.

Briefly, FIG. 1A shows generation of pDM138 and various virus specific reporter constructs. p138 was created from pDM128 by the deletion of 1.2 kb including RRE followed by insertion of unique ClaI site. Response elements from various complex retroviruses were then inserted generating species specific reporters for Rev-like protein function.

FIG. 1B illustrates the versatility of this system by showing several examples of the generation of specific reporters. Briefly, FIG. 1B shows the induction of CAT activity by the addition of Rev-like proteins. Results of CAT analysis of transactivation by various Rev-like proteins. The presence (+) or absence (−) of corresponding transactivator is indicated. p138 is a basic vector with no response element. Specific responses are for: HIV; HTLV, SIV (simian immunodeficiency virus); EIAV (equine infectious anemia virus); and MS2 (heterologous fusion protein system utilizing the bacteriophage RNA binding protein MS2). Insertion of the response elements from complex retroviruses such as, HIV, HTLV, SIV, and EIAV allows the generation of specific reporters for the function of the corresponding Rev-like protein. In each case, there is a specific 30-100 fold induction of the export of intron containing mRNA in the presence of the appropriate posttranscriptional transactivator. We generated a heterologous system utilizing the specific RNA protein interaction of the bacteriophage coat protein MS2. When fused to a Rev-like protein, it can activate a derivative of pDM138 containing MS2 binding sites (See, e.g., McDonald D., et al., J. Virol., 66:7232-7238 [1992]). These studies indicate that this assay system can be used to study various aspects of the pathway utilized by retroviruses to facilitate the nuclear export of viral RNA. FIG. 1C shows that the assay can also detect cis-acting sequences which interact with cellular factors involved in RNA export such as the posttranscriptional regulatory element (PRE) of the hepatitis B virus. (See e.g., Donnello J. E., et al., J. Virol., 70:4345-4351 [1996]). In FIG. 1C HBVPRE is shown to stimulate the localization of unspliced RNA to the cytoplasm when present in the sense orientation. Derivatives of pDM138 were generated that contain the HBVPRE in sense and anti-sense orientation. CAT activity is induced 15 fold when the HBVPRE is present in the correct orientation.

To generate a specific reporter for BLV Rex, we inserted a fragment encompassing the BLV Rex responsive element (BxRE) generated by PCR. By analogy to the HTLV, the response element should be located within the repeat (R) region of the proviral long terminal repeat. Consistent with this hypothesis, a BLV Rex responsive sequence has previously been detected in the R region (Felber B. K., et al., New Biol., 1:318-28 [1989]). To test the functionality of this reporter we determined the expression of CAT enzyme in response to the expression of BRex, HRex, and HIV Rev. This analysis revealed that a sensitive assay for BRex function had been generated.

Example II

Creation of a Packaging Cell and Vector Propagation

This example describes experiments designed to produce packaging cell lines and propagation of the antiviral constructs described herein. An antiviral construct, as disclosed herein, is transfected into a cell line (e.g., 293GP) using calcium phosphate precipitation. The 293GP cell line is selected to provide the Gag and Pol proteins needed for production of the replication defective viral particle. At the same time as this initial transfection, the VSV-G envelope gene (driven by a CMV promoter) is also transfected into the cell line. This step allows infectious replication defective retroviral particles containing the gene construct of interest to be produced. These particles are used to re-infect the cell line. This process results in a single copy of the provirus integrated into the packaging cell genome. After infection, single cells are plated into 96 well plates and cultured for two weeks until colonies form.

Vector development is optimized by selecting high titer clonal lines that secrete the protein of interest into the cell culture medium an verification of the protein produced. Selection alone does not guarantee that the protein produced is the desired product, as there could be rearrangements or mutations in the region of the vector coding for the target protein. In this case, the desired protein (e.g., BRex or HRex) will not be secreted prompting development of the following alternative strategies.

Cells are selected (e.g., using neo or GFP) giving rise to clonal lines that are known to contain an inserted vector backbone of interest. Resulting clonal lines are expanded to a point where the BRex protein can be detected in cell lysates with a polyclonal antibody against the protein of interest (e.g., Rex). This can be done directly in microtiter plates where the cells are growing. To pass this screen the clonal cell lines must: 1) express the Rex protein; and 2) the Rex protein produced must be of the expected and appropriate size. Accordingly, synthesis of a peptide corresponding to the NES region of TD BRex or TD HRex is accomplished, and antibodies to this peptide are produced using techniques well known in the art or by requesting production of antibody from a commercial service.

After expansion, a portion of the cells in each colony are passed to a second plate and transfected with VSV-G to produce replication defective virus which is then used to infect a constant number of 208 rat fibroblast cells. These infected cells are grown for three days and the media is assayed for production of the protein of interest. The highest protein production is directly correlated to the cell line that produces the highest titer virus. The cell line exhibiting the highest titer is then used for all subsequent experiments and a master stock and working cell bank of this line is established. The selected cell line is expanded for large-scale replication defective virus production.

Example III

Vector Evaluation

Vectors are evaluated using D17 cells which have also served as a model system for studying BLV (Boris-Lawrie et al., J Virol 71(2):1514-20, 1997). Stable cell lines of D17 cells transduced with retrovectors have been established. As a source of BLV virus to infect these cell lines, BL3.1 and FLK cells have been established in culture. The FLK cells produce BLV at higher titer than the BL3.1 cells and have proven more reliable in infecting new cells.

BLV replication is measured by two assays. The first is an assay for reverse transcriptase enzymatic activity, which is commercially available (Roche). Briefly, samples of media are centrifuged to remove whole cells and cellular debris. Following lysis of the viral particles with detergent, a primer template is added and the incorporation of digoxigenin and biotin labeled nucleotides are incorporated into the reverse transcribed cDNA product. The level of product is measured by ELISA. The second assay also looks at virus particles that from culture media. In this case, primers specific for a region of the BLV Pol gene are added and reverse transcribed into cDNA. The amount of cDNA product is measured by real-time PCR. The advantage of real-time PCR is that an estimate of titer can be obtained over several orders of magnitude. A standard curve using plasmid DNA indicates that BLV can be estimated from 10E1 to 10E7 in the same assay. The following results are from a similar assay with Bat Lung Cells.

Quantity of BLV infected cells: The number of BLV-provirus carrying bovine lymphoblast cells is detected using a quantitative PCR assay for tax and pol as evidence of provirus infection. This PCR assay detects cell associated BLV DNA.

Figure 21:
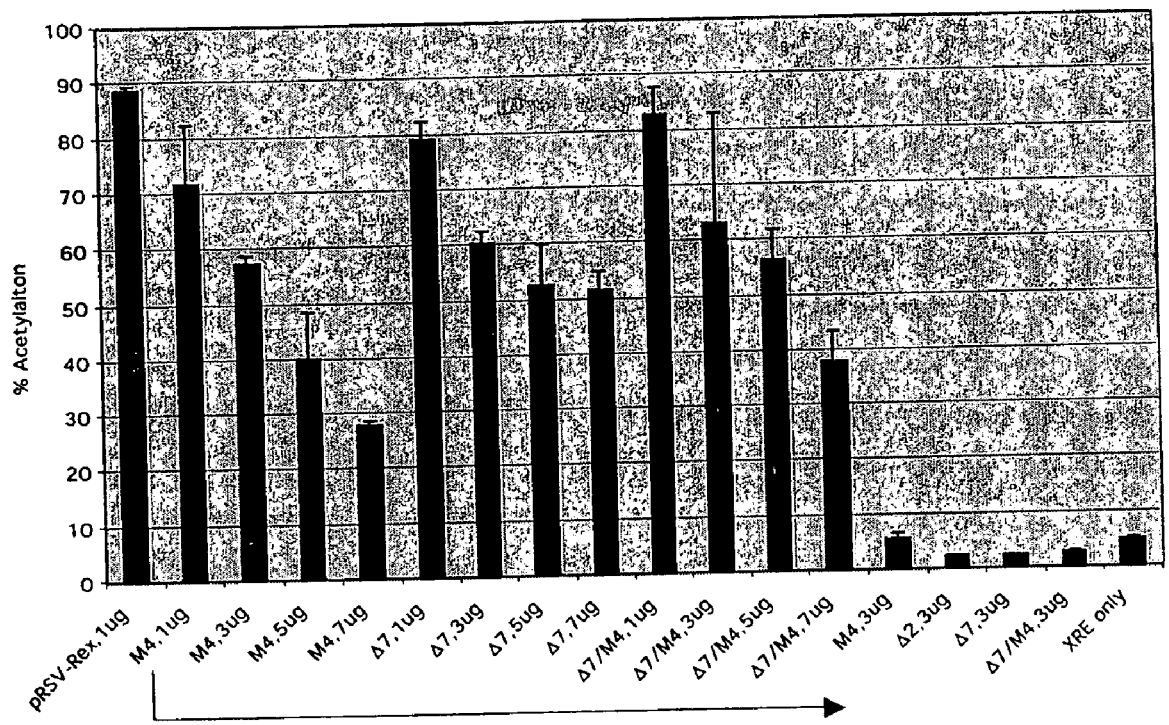
FIG. 21 provides a graphical comparison of the TD mutant activity of various mutants.
Figure 27A:
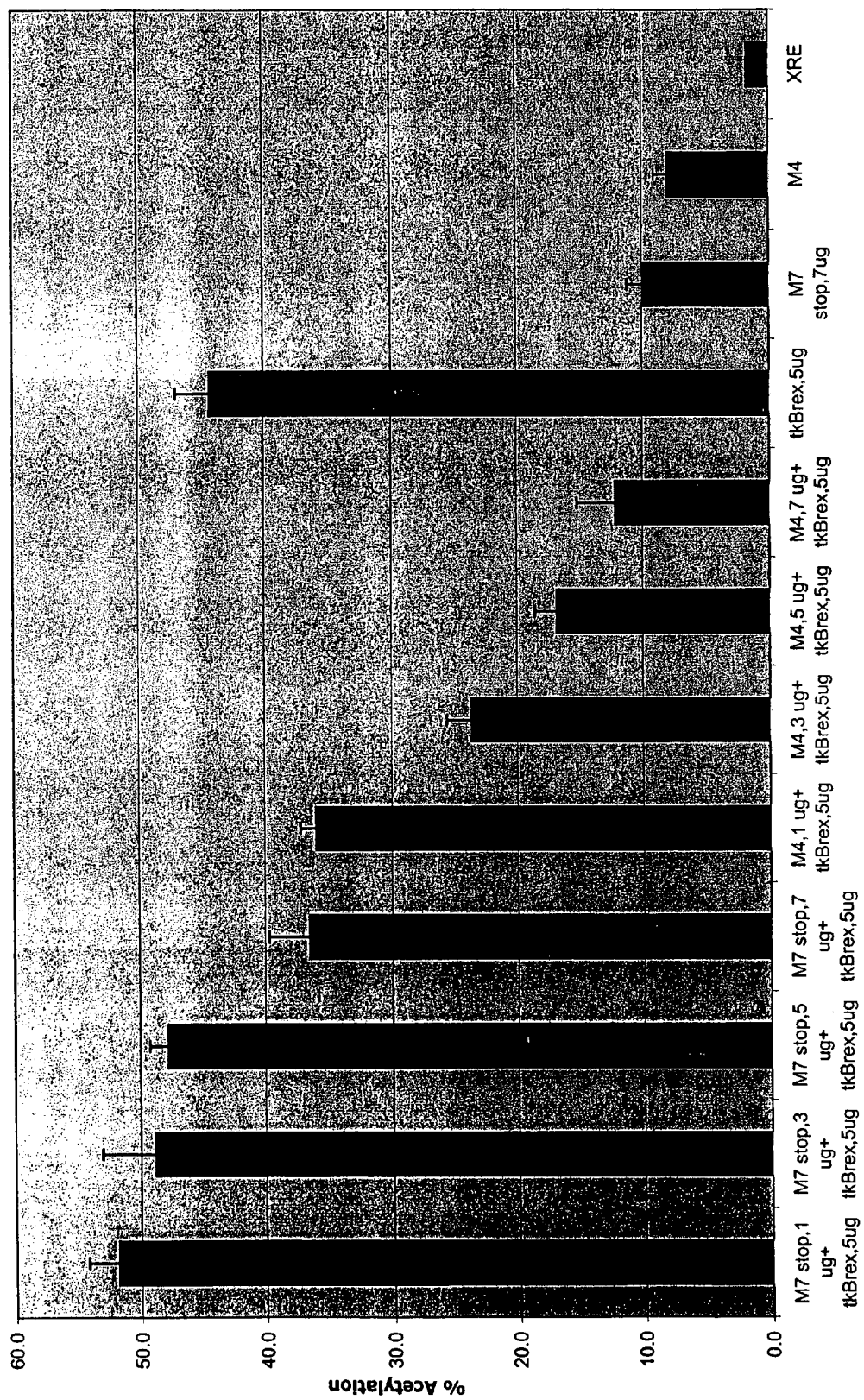
FIG. 27 shows that M4 prevents induction of BLV replication using a PCR assay.

Tax and Pol transcription: Virus replication is quantified using a RT-PCR assay for tax and pol in combination with mimics (See, Pyeon, D., and Splitter, G. A., J. Virol., 72:6917-6921 [1998]). Comparing transcription levels of tax and pol in transfected versus non-transfected cells will assess the ability of TD BRex and TD HRex to inhibit virus replication in bat lung cells. Transcription of tax will assess expression of this proviral gene that is often expressed without virus replication. Transcription of pol is necessary for production of full-length viral transcripts and indicates virus replication. In performing RT-PCR assays, the removal of proviral DNA is routinely tested, following DNAase treatment in every RT-PCR assay by performing a PCR assay before reverse transcription. tax and pol transcription are quantified as described in FIG. 5. Briefly, in FIG. 5 plasmids containing mimics for tax (450 bp) or pol (700 bp) were generated using primers and an internal nonspecific stuffer region followed by cloning the mimic fragment into the plasmid. Also, plasmid standards for tax and pol were generated using the respective primers and BLV-infected cells in an RT-PCR reaction, followed by cloning the fragments into plasmids. Serial two-fold plasmid standards were diluted for tax (691 bp) and pol (530 bp) and fixed amounts of mimic plasmid were added to the same tube and amplified simultaneously. The standard reaction for tax is shown in FIG. 5A. Gel photographs were scanned and the amplified DNA bands analyzed by densitometry using the NIH Image program version 1.61 with standard curves, FIG. 5B. Similarly, pol plasmid standards and mimics were amplified, FIG. 5C, and standard curves determined, FIG. 5D. Using this methodology, the amount of tax or pol transcription from BLV-infected cells isolated from animals was determined by comparing the density ratios of sample reactions and mimic reactions to the standard curve.

Example IV

Other Systems for Evaluating the Effectiveness of the Antiretroviral Vectors Several additional models are available to evaluate the efficacy of the disclosed antiviral constructs to deliver TD Rex protection from infection by complex retroviruses like BLV, HTLV-1 and HTLV-2. For example, the SCID bo mouse has an immune system reconstituted by bovine lymphocytes that lends itself to study of early stages of BLV infection. An ovine model for BLV disease is also available (See, Gatei M. H., et al., Zentralbl Veterinarmed, [B] 36(9): 652-60 [1989]) that shows more rapid progression than natural bovine disease.

Example V

Analysis of TD Mutants by RNA Export Assay

The RNA export assay described in Example 1 was used to analyze a number of potential transdominant negative mutants. The first set of mutants analyzed are depicted in FIG. 17. Quantitative analysis of trans-inhibition by these mutants is graphically depicted in FIGS. 18A and 18B. As can be seen, all mutations showed compromised function except M5, which turned out to be wild-type. M4 showed the least activity and was tested for the ability to inhibit the wild-type protein. One microgram of wild-type Brex was transfected alone or with increasing amounts of M4 Brex. Dose dependent inhibition was observed. A seven-fold excess of M4 inhibited wild-type protein function by 80%.

Additional point and deletion mutants were then tested. These mutants are depicted in FIG. 19. Quantitative analysis of trans-inhibition by these mutants is graphically depicted in FIG. 20. As can be seen, deletion mutant M7 also showed low activity. Therefore, double mutants were made and tested. The results of these experiments are depicted graphically in FIG. 21. Although deletion mutant Δ7 and double mutant Δ7M4 have low activity by themselves, they showed less activity to inhibit 1 microgram of wild-type Brex compared to M4. These results indicate that amino acids 119 and 120 of Brex are the most sensitive to dominant negative mutations.

Figure 22B:
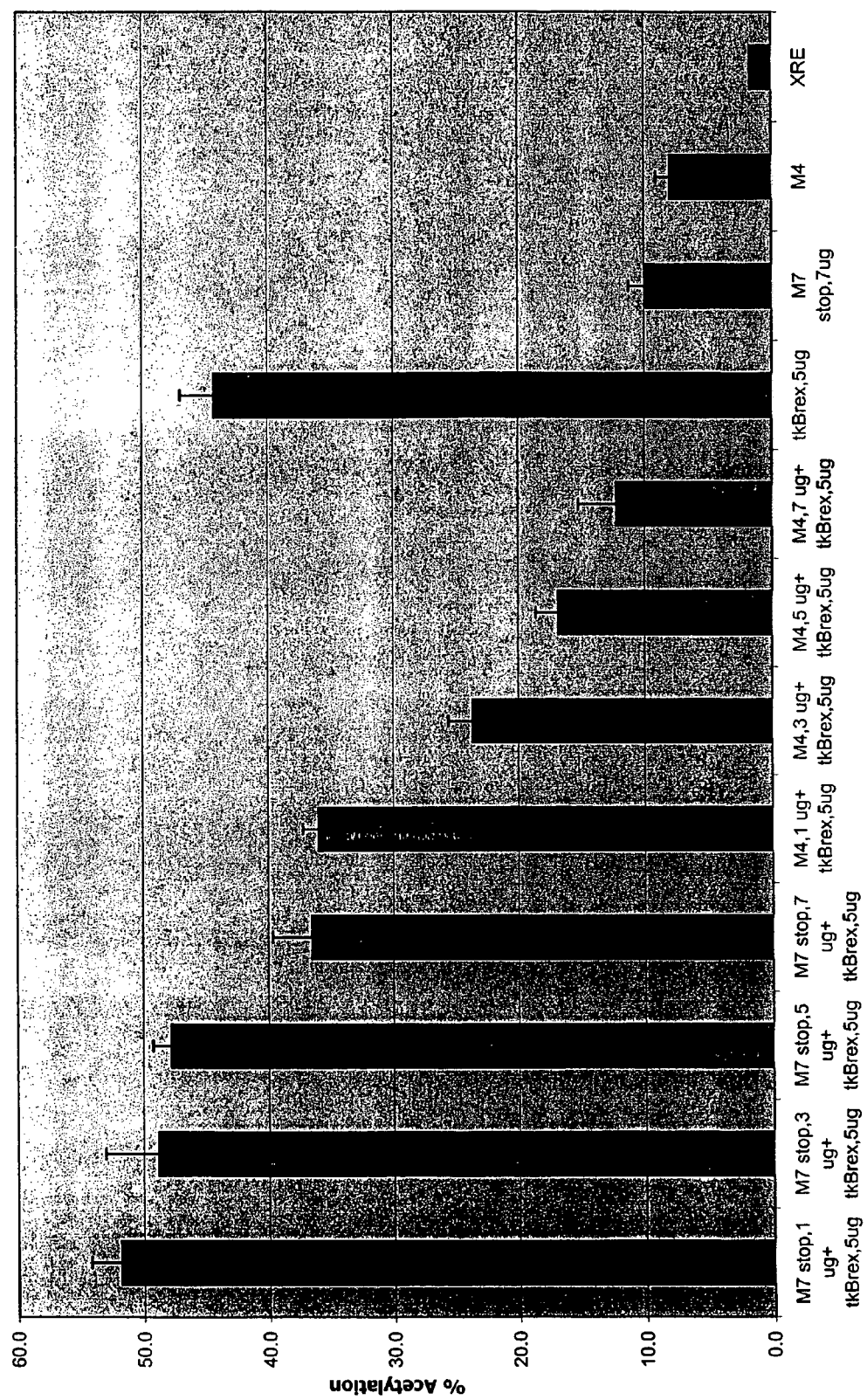
FIGS. 22A, B, and C providess a graphical comparison of the TD mutant activity of M7stop, M4, and M4Δ7.
Figure 72C:
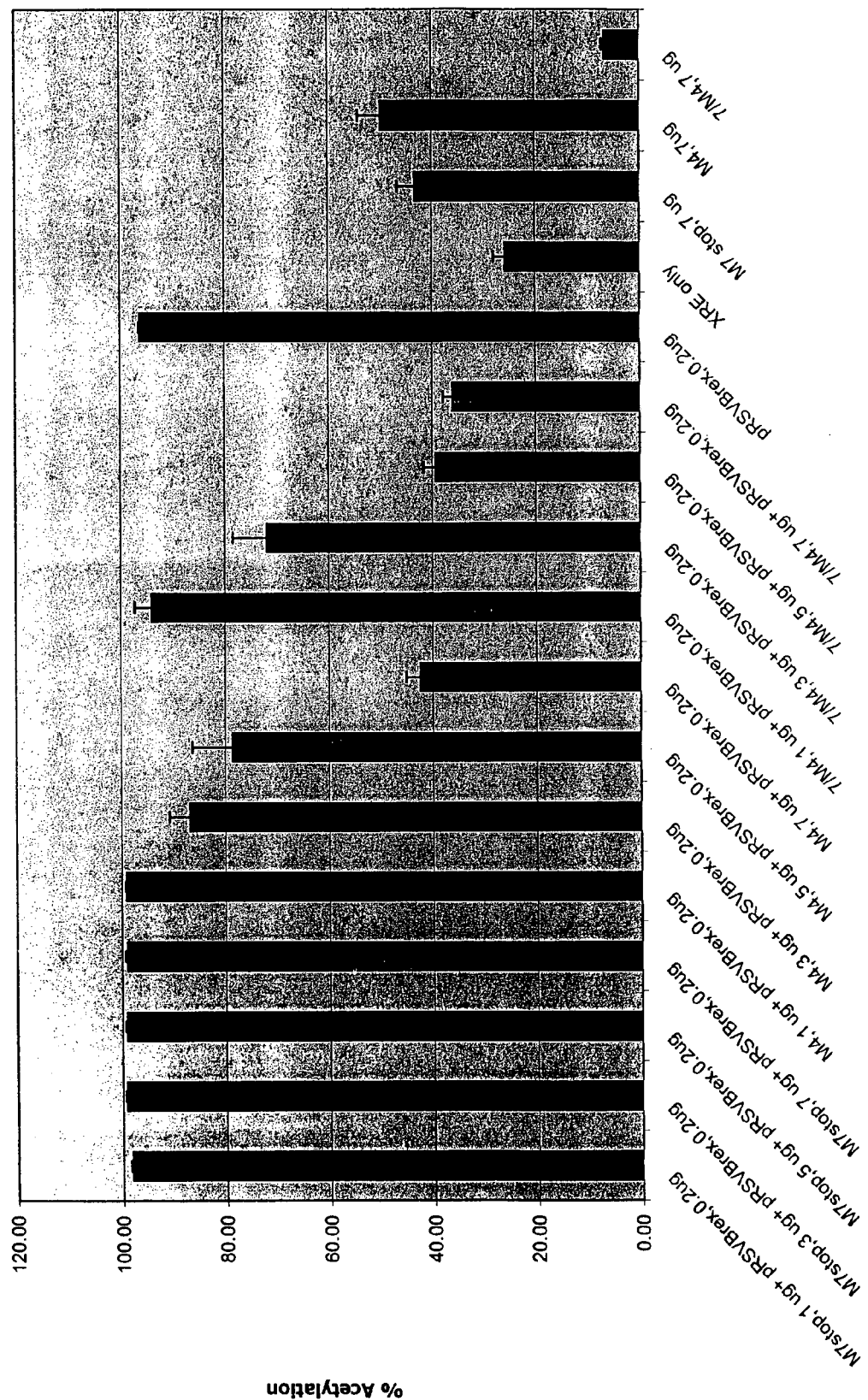

FIGS. 22A, B, and C, provides additional comparisons of mutants M4 (SEQ ID NO:5), M7stop (SEQ ID NO:7; see also FIG. 18) and Δ7M4.

Example VI

Inhibition of Induction of BLV Viral Replication

This Example describes the inhibition of induction of BLV viral replication by a trans-dominant mutant of BLV Rex protein.

A. Methods

DNA Constructs pBLV913 comprises a genomic clone of the BLV provirus isolated from fetal lamb tissue. The sequence is essentially the same as GenBank accession number K02120. pBLV913 was used as the template to PCR clone the Tax gene. pREV-TetOn was purchased from ClonTech. pLHTre-G contains the Gateway RfA recombination fragment cloned into pREV-TRE (ClonTech) at the Hind III and Cla I sites. pENT-Btax contains the BLV Tax gene that was PCR amplified from pBLV913 using primers BTax5

```
5' GGG GAC AAG TTT GTA CAA AAA       (SEQ ID NO: 15)
AGC AGG TCT CCG CCG CCA CCA TGG
CAA GTG TTG TTG GTT GGG G 3'
``` and BTax3

```
5' GGG GAC CAC TTT GTA CAA GAA AGC   (SEQ ID NO: 16)
TGG GTC TCA AAA AAG GCG GGA GAG C
3'.
```

The PCR product was cloned using BP Clonase (InVitrogen) into pDONOR201, and clones were confirmed by DNA sequencing.

pLHTre-Btax contains the BLV Tax gene recombined using LR Clonase (InVitrogen) into the pLH-TreG retrovector plasmid. pRS-BrexM4//pRS-BRex are plasmids with M4 mutant and wild-type BLV Rex genes. pENT-M4 contains a 532 bp EcoRI-Xho I fragment that was isolated from pRS-BRexM4 and ligated to pENT-Nco which had been digested with EcoRI and Xho I. pENT-Nco is a modification of the pENTR11 which has had the Nco I cloning site deleted to remove an extra ATG which is upstream of the initiation codon of the desired mRNA Nco site deleted by opening with Nco I, treating with Mung Bean Nuclease and re-ligating. pENT-Rex contains the Cla I-Xho I fragment of wild type Rex that was removed from pRS-BRex plasmid and ligated into the Cla I/Xho I sites of pENT-M4.

BLV Promoter Constructs pUC-BLV3 contains the 3' LTR from BLV913 cloned into pUC19 to simplify cloning of the U3 portion of the LTR (BLV promoter). The 799 bp EcoRI-Kpn I fragment of pBLV913 (GD2400) containing the 3' LTR was excised by restriction digestion and fragment purified. This was ligated into pUC19(GD0069) which had been digested with Eco RI and Kpn I, and fragment purified.

pLN-BLV is 6169 bp and places the 3' LTR promoter from pBLV913 into the pLN-MCS retroviral backbone. The plasmid pLN-MCS was digested with Avr II and Stu I. The plasmid pUC-BLV3 was digested with Sac I, treated with Mung bean nuclease to remove the 3' overhang, re-digested with Nhe I (compatible sticky end with Avr II) and the 345 bp fragment was gel purified.

pLNBlv-G contains the Gateway RfA element cloned into the retroviral vector pLN-BLV. The pLN-BLV DNA was digested sequentially with Hind III and Cla I. The fragment purified DNA for the Hind III—Cla I Gateway RfA fragment was isolated from pLNC-G.

Cloning

The plasmid pBLV913 contains a genomic clone of the BLV provirus isolated from fetal lamb tissue. The BLV viral sequence is essentially the same as GenBank: (Accession K02120). The pBLV913 plasmid was used to clone a BLV responsive promoter from the 3' LTR and the wild-type BLV Tax gene.

Retrovector plasmids were converted to pseudotyped retrovector by transient CaPO4 transfection of the plasmid DNA and pHCMV-G (VSV-G envelope expressing plasmid using the CMV promoter) into a 293 Gag-Pol packaging cell line.

Results

These experiments investigated whether or not a trans-dominant negative mutant of BLV Rex could inhibit BLV viral replication, and thus prevent progression to disease in transgenically modified animals. Trans-dominant negative mutants of BLV Rex were created by mutating amino acids analogous to those found in HTLV Rev, which have been found to create inhibitory proteins. One mutant—M4—was found to inhibit wild type Rex function as much as 80% in an in vitro assay which measured Rex-dependent export of unspliced RNA from the nucleus. This mutant was cloned into a retrovector expression system where Rex M4 expression was under the control of the strong constitutive CMV promoter.

Figure 23:
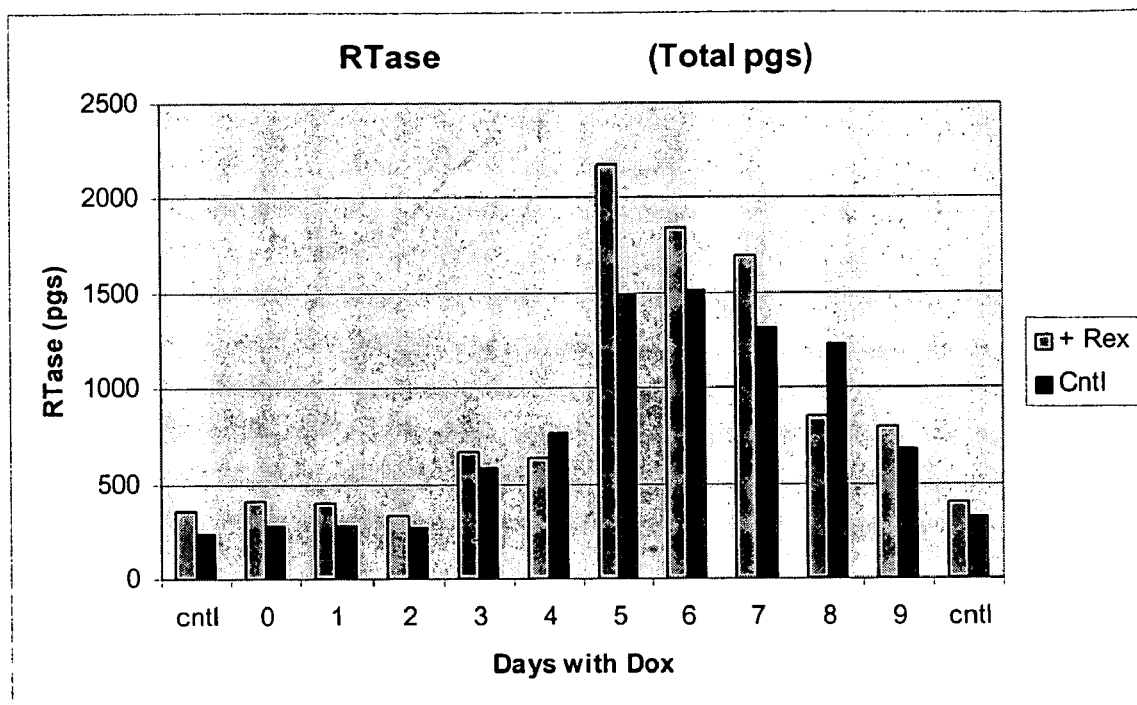
FIG. 23 shows that BLV replication is induced in D17 TetOn Tax BLV cells by Dox using a reverse transcriptase assay.
Figure 24:
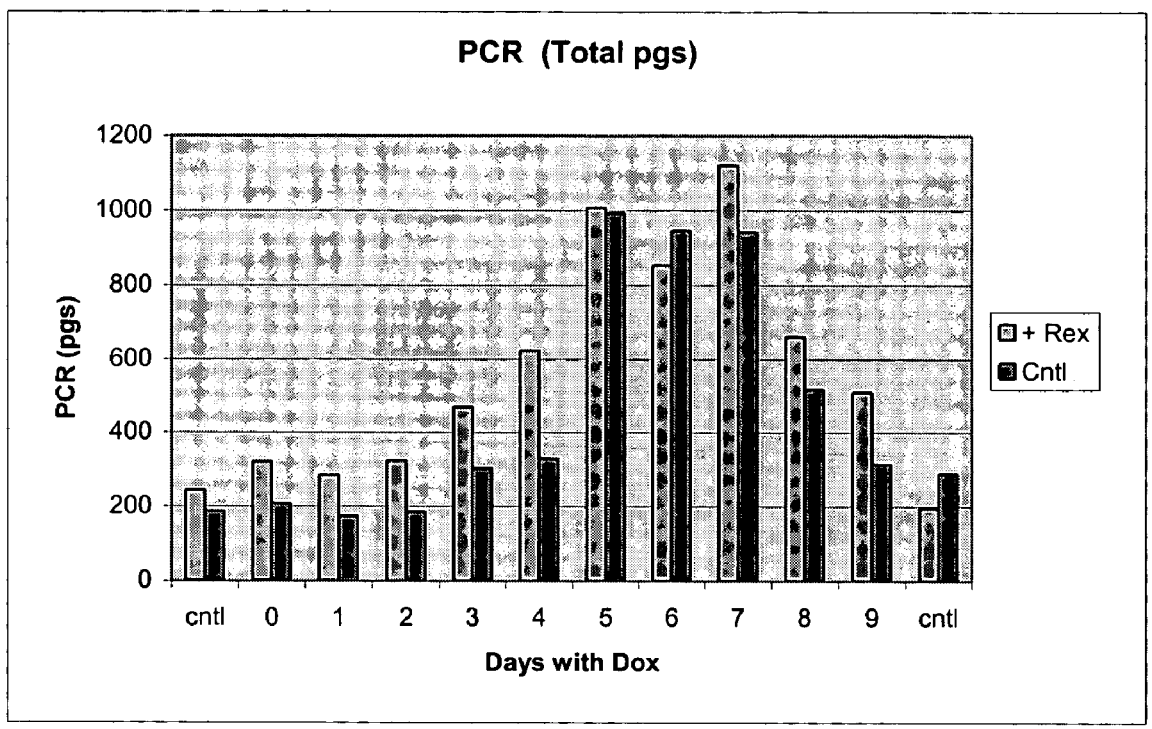
FIG. 24 shows that BLV replication is induced in D17 TetOn Tax BLV cells by Dox using a PCR assay.

FIGS. 23 and 24 show the establishment of a cell line that induces BLV replication. D17 cells were modified with the pREV-TetOn retrovector (ClonTech) to establish expression of the reverse Tet-controlled transactivator protein in cells. The cells were further modified with the BTax gene under control of the TRE promoter by transduction with LHTre-BTax retrovector and clonal cell lines were isolated. TetON control of the BTax gene was evaluated by transiently transfecting the reporter plasmid pBLV-YFP. The cell line was infected with BLV by incubation with FLK supernatant in the presence of 10 μg/ml polybrene. Clonal lines were selected to ensure all cells were uniformly infected with BLV and were confirmed by Southern blot for BLV insertion into genomic DNA. Cultures were split into 6 flasks and on successive days Dox (Doxycycline) was added to one flask of each set. After 5 days in culture, supernatant was collected from flask and assayed for RTase enzyme activity (FIG. 23) and BLV RNA using real-time PCR (FIG. 24). The addition of Dox to D17 TetOn BLV cells gave ~5 fold increases in RTase activity and BLV RNA measured in cell-free media supernatant. After ~7 days, the TetOn system begins to lose the ability to induce BLV replication.

Figure 25:
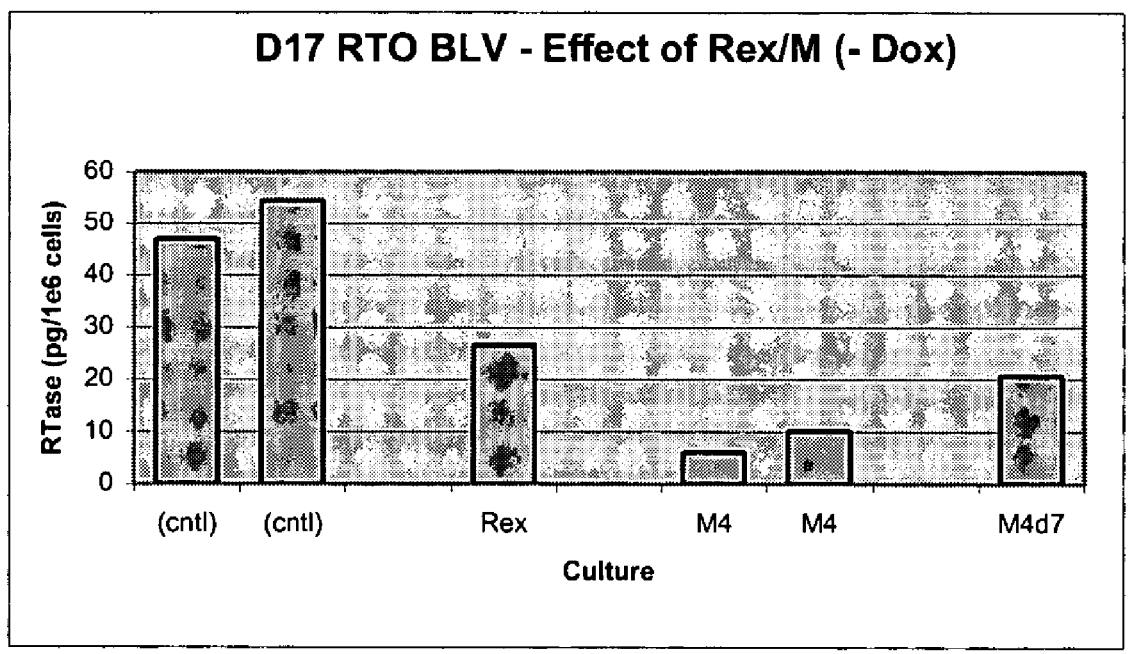
FIG. 25 shows the effect of Rex and M4 on Basal replication in D17 TetOn Tax BLV cells.

FIG. 25 shows the effect of Rex and M4 on Basal replication in D17 TetOn Tax BLV cells. Transduction with LBC-M4W reduces baseline activity of BLV replication in D17 TetOn BLV cells in the absence of Dox.

Figure 26:
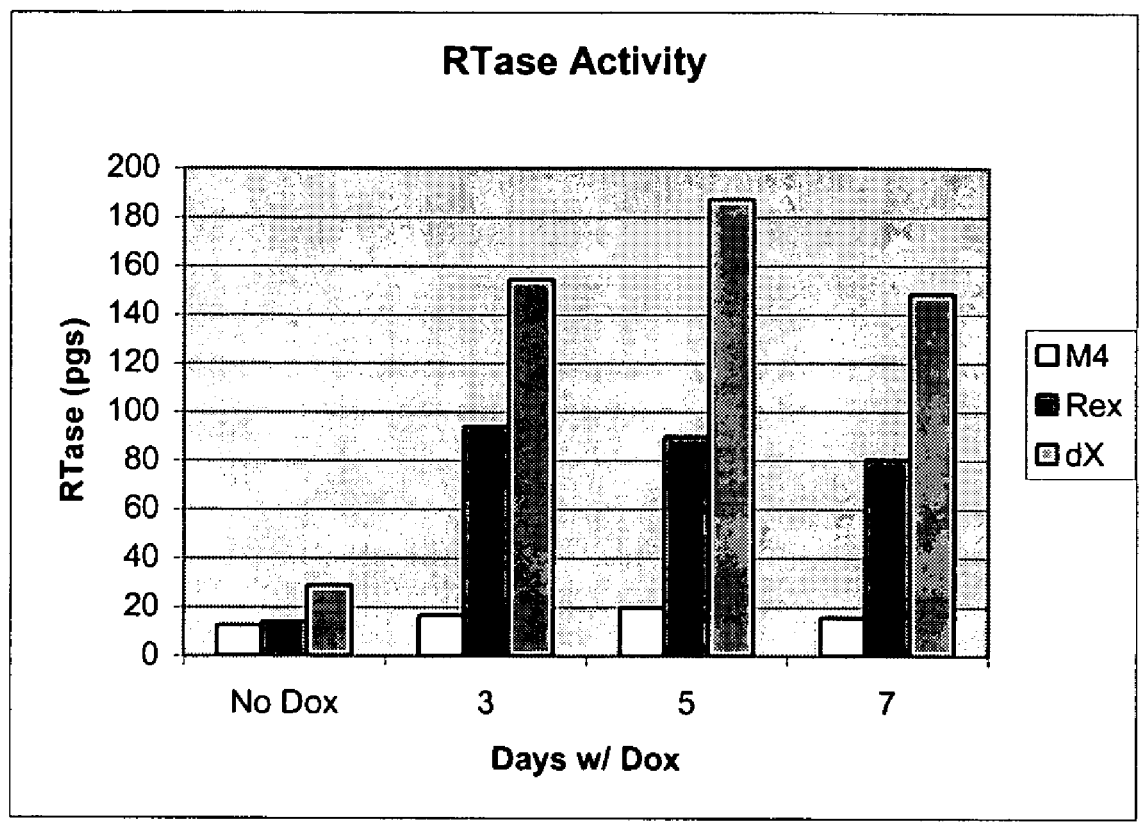
FIG. 26 shows that M4 prevents induction of BLV replication using a reverse transcriptase assay.
Figure 27:
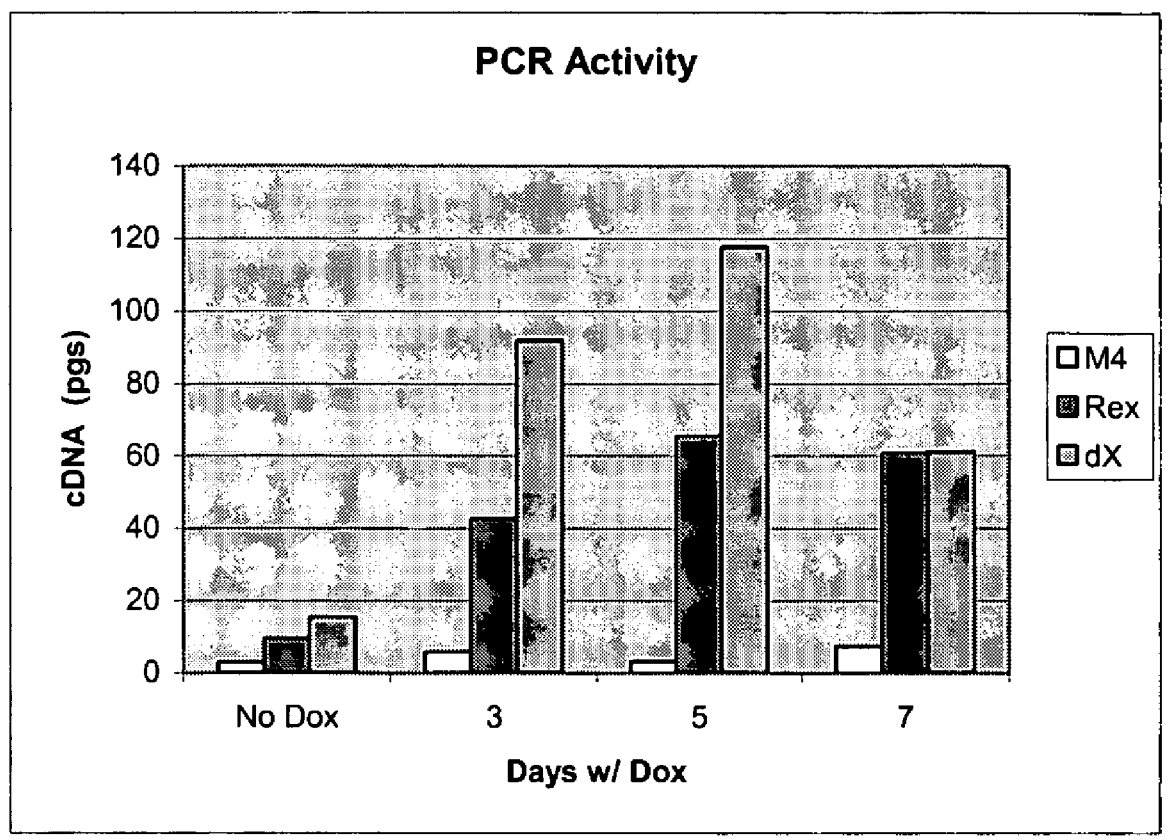
Figure 28:
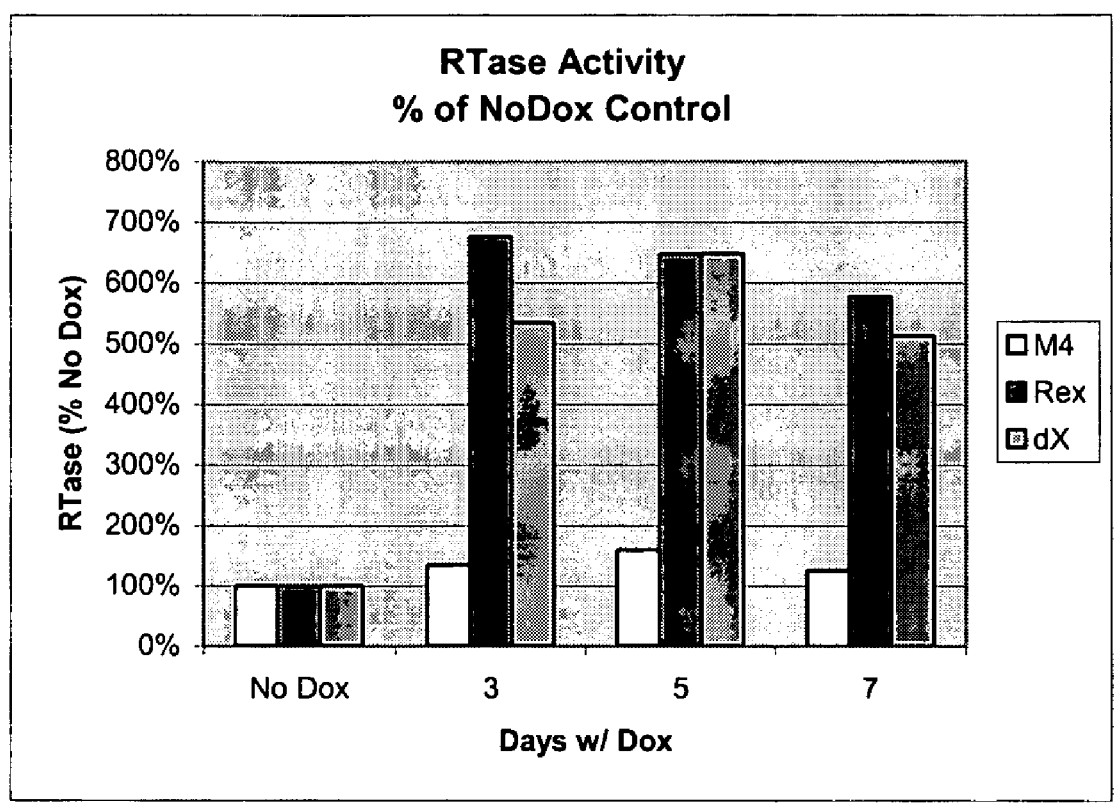
FIG. 28 shows that M4 prevents induction of BLV replication (expressed as % No Dox—fold increase in BLV replication in M4 cells is much less than Rex or control (dX)) using a reverse transcriptase assay.
Figure 29:
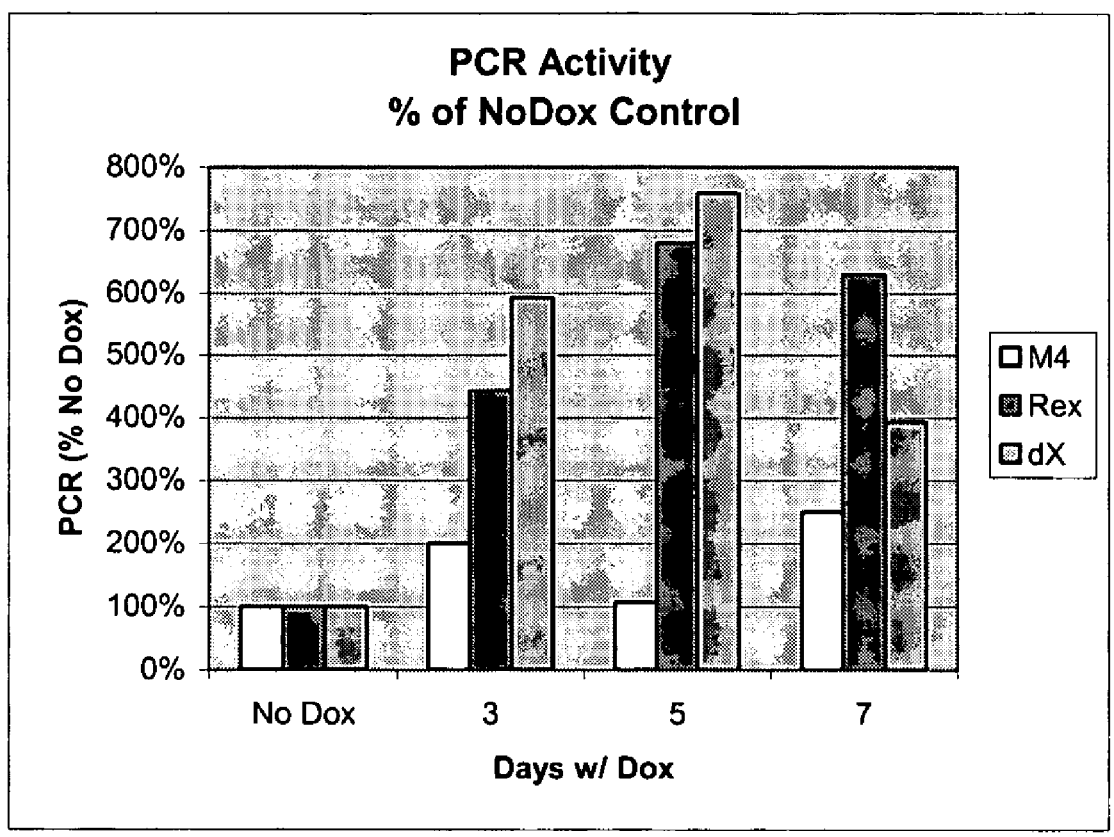
FIG. 29 shows that M4 prevents induction of BLV replication (expressed as % No Dox—fold increase in BLV replication in M4 cells is much less than Rex or control (dX)) using a PCR assay.

FIGS. 26 and 27 shows that M4 prevents induction of BLV replication. FIGS. 28 and 29 show that M4 prevents induction of BLV replication as expressed as % No Dox. The fold increase in BLV replication in M4 cells is much less than Rex or control (dX).

Figure 30:
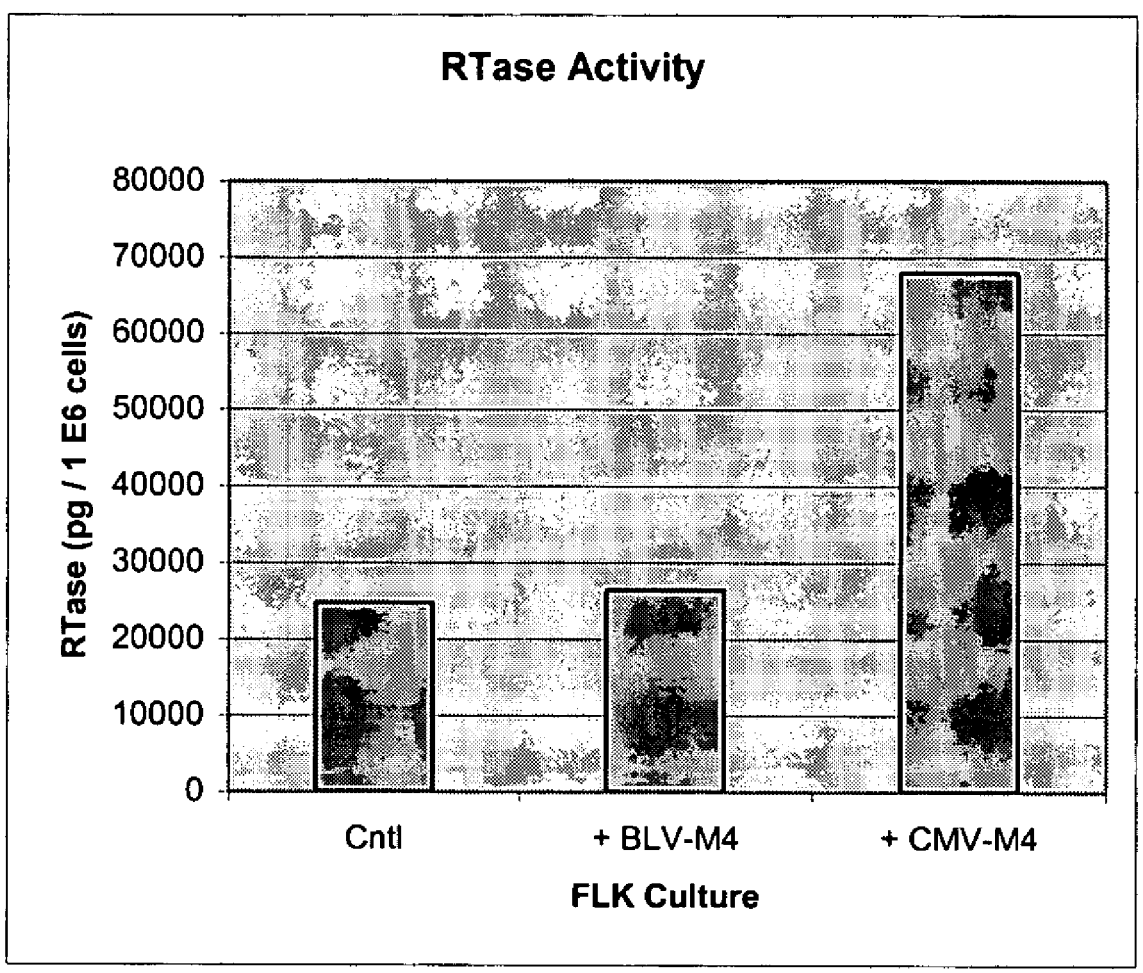
FIG. 30 shows M4 enhances viral replication in FLK cells.

FIG. 30 shows M4 enhances viral replication in FLK cells. The present invention is not limited to a particular mechanism. Indeed, an understanding of the present invention is not limited to an understanding of the present invention. Nonetheless, it is contemplate that, given that FLK cells have very high replication (20,000 pg/1E6 cells over ~7 days vs 50-100 for D17 TetON Tax), adding CMV-M4-W increases viral replication.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A non-human host cell comprising a genome, said genome comprising a gene encoding a transdominant negative mutant of the bovine leukemia virus BLV Rex protein, wherein said transdominant negative mutant of the BLV rex protein is encoded by a nucleic acid selected from the group consisting of SEQ ID NOs: 5 and 7.

2. The host cell of claim 1, wherein said genome is a bovine genome.

3. A nucleic acid encoding a transdominant negative mutant of a BLV Rex protein, wherein said transdominant negative mutant of the BLV rex protein is encoded by a nucleic acid selected from the group consisting of SEQ ID NOs: 5 and 7.

4. The nucleic acid of claim 3, further comprising vector sequences.

5. A vector comprising a promoter operably linked to a nucleic acid encoding a transdominant negative mutant of a BLV Rex protein, wherein said nucleic acid is selected from the group consisting of SEQ ID NOs: 5 and 7.

6. The vector of claim 5, wherein said vector is a retroviral vector.

7. The vector of claim 6, wherein said retroviral vector is a pseudotyped retroviral vector.

8. The vector of claim 6, further comprising a nucleic acid sequence encoding a cell surface antigen.

9. The vector of claim 8, wherein said sequence encoding a cell surface antigen is arranged in a polycistronic sequence with said nucleic acid encoding a transdominant negative mutant of a BLV Rex protein.

10. The vector of claim 5, wherein said promoter is a BLV U3 promoter.

11. The vector of claim 9, wherein transcription of said polycistronic sequence is driven by the BLV U3 promoter.

* * * * *